United States Patent [19]
Brill, III et al.

[11] Patent Number: 4,597,294
[45] Date of Patent: Jul. 1, 1986

[54] ULTRASONIC NONDESTRUCTIVE TUBING INSPECTION SYSTEM

[75] Inventors: Bernard A. Brill, III, Bellevue; Warren R. Junker, Monroeville; John K. White, Bethel Park; Iftikhar A. Rana, East Pittsburgh; Bruce W. Bevilacqua, Irwin; Frank W. Cooper, Jr., Monroeville; Bruce J. Taszarek, Mt. Lebanon, all of Pa.

[73] Assignee: Westinghouse Electric Corp., Pittsburgh, Pa.

[21] Appl. No.: 624,078

[22] Filed: Jun. 25, 1984

[51] Int. Cl.$^4$ ............... G01N 29/04; G21C 17/00
[52] U.S. Cl. .................................... 73/623; 73/640; 376/252
[58] Field of Search ............... 73/623, 640; 181/102, 181/104, 105; 367/27; 376/252

[56] References Cited

U.S. PATENT DOCUMENTS

| | | | |
|---|---|---|---|
| 3,553,640 | 1/1971 | Zemanek, Jr. | 367/27 |
| 3,810,384 | 5/1974 | Evans | 73/623 |
| 4,037,465 | 7/1977 | Cook | 73/623 |
| 4,096,757 | 6/1978 | Ishii et al. | 73/623 |
| 4,212,207 | 7/1980 | Conradi | 73/623 |
| 4,361,044 | 11/1982 | Kupperman et al. | 73/623 |
| 4,388,831 | 6/1983 | Sherman | 73/623 |

OTHER PUBLICATIONS

Westinghouse Disclosure NSD-80-23.
Westinghouse Disclosure NSD-82-05.

Primary Examiner—Howard A. Birmiel
Attorney, Agent, or Firm—L. A. DePaul

[57] ABSTRACT

An apparatus is disclosed for inspection of tubing, and more particularly, the determination of the extent of erosion in the wall of a heat exchange tube of a nuclear reactor. An ultrasonic transducer assembly is movable axially and rotatably in a helical path for producing both thickness and position signals to provide a map of wall thickness.

12 Claims, 16 Drawing Figures

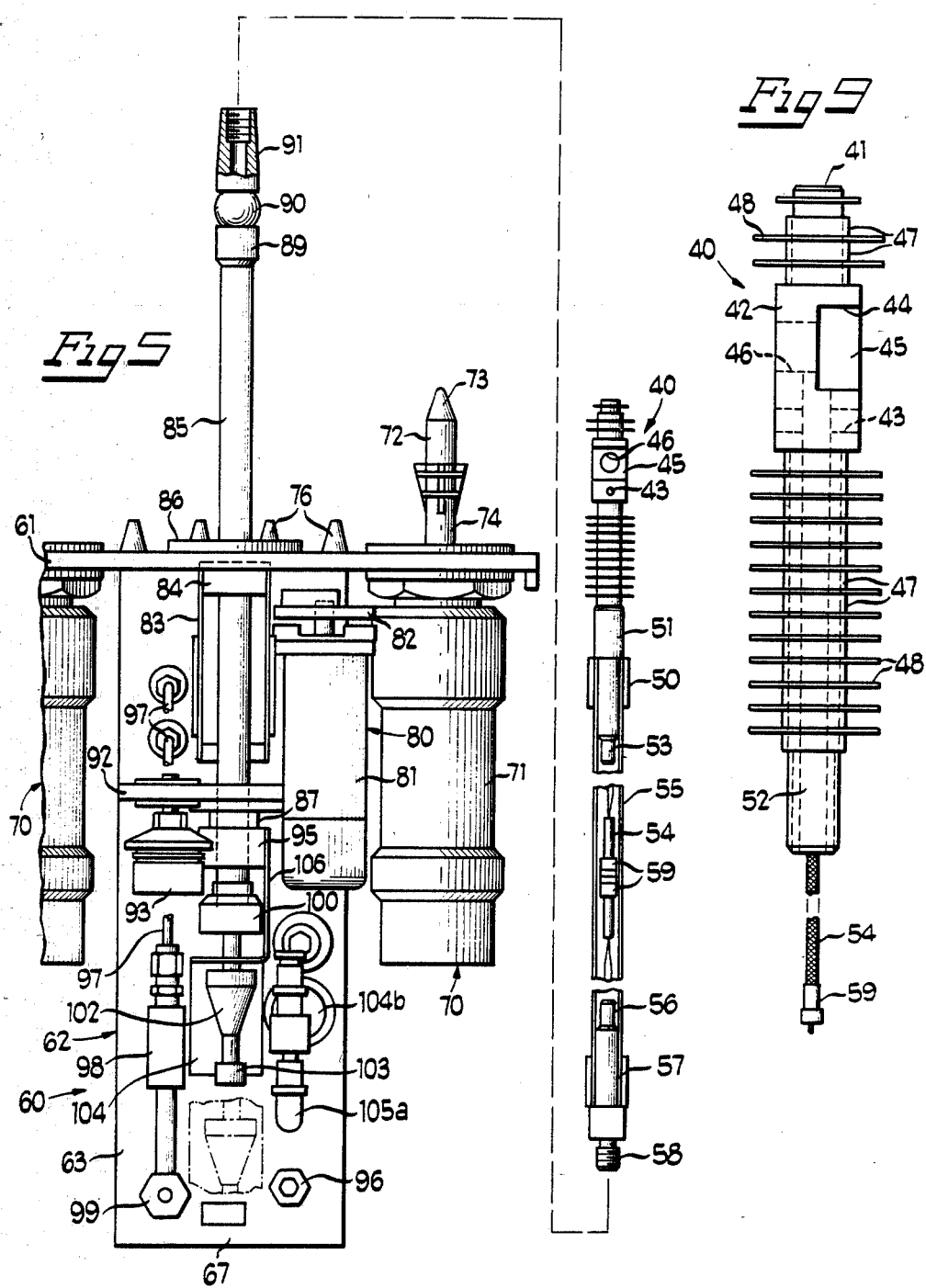

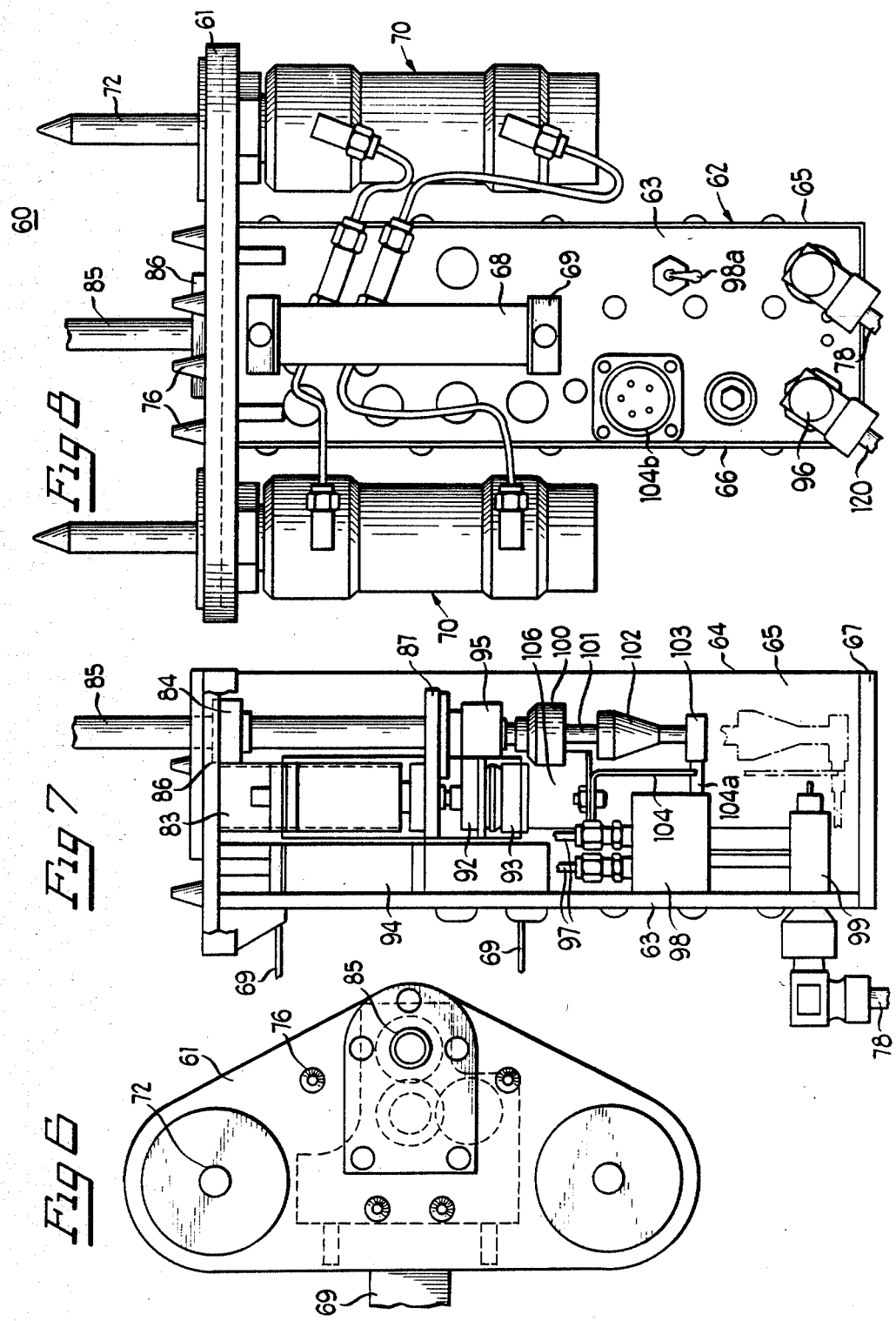

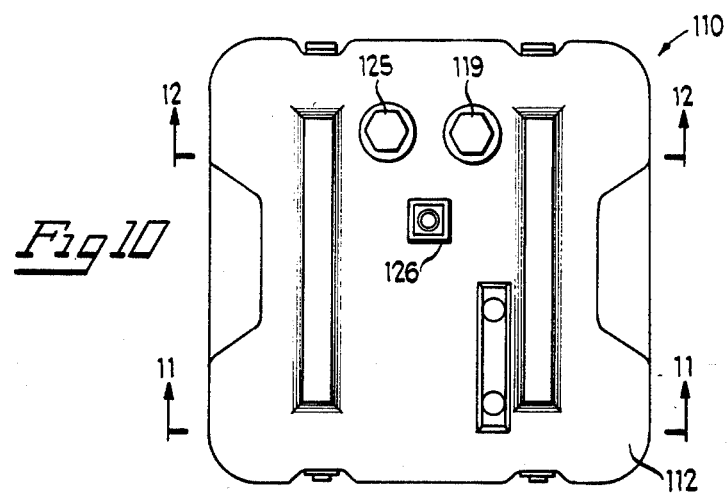
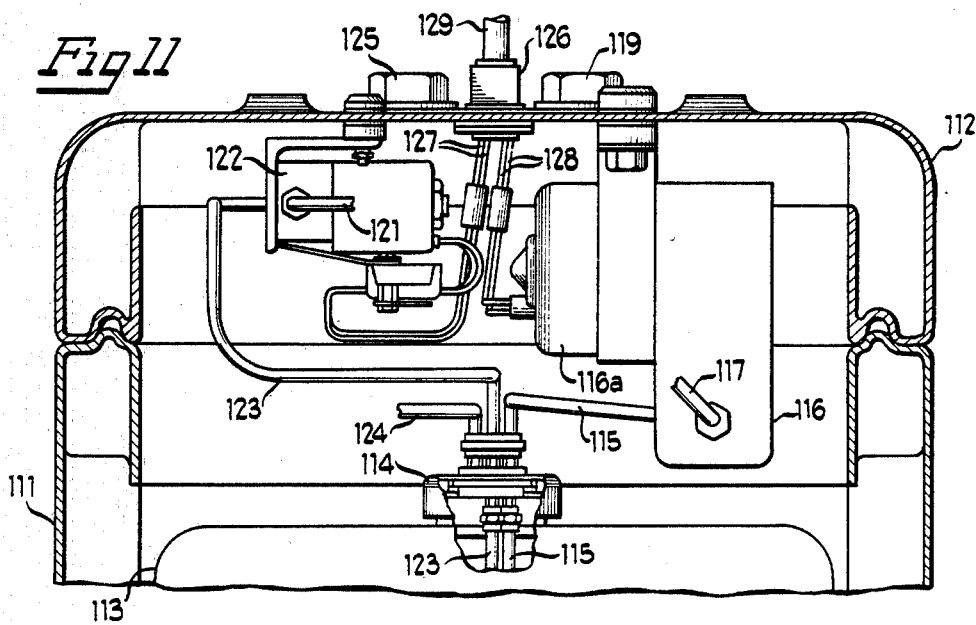
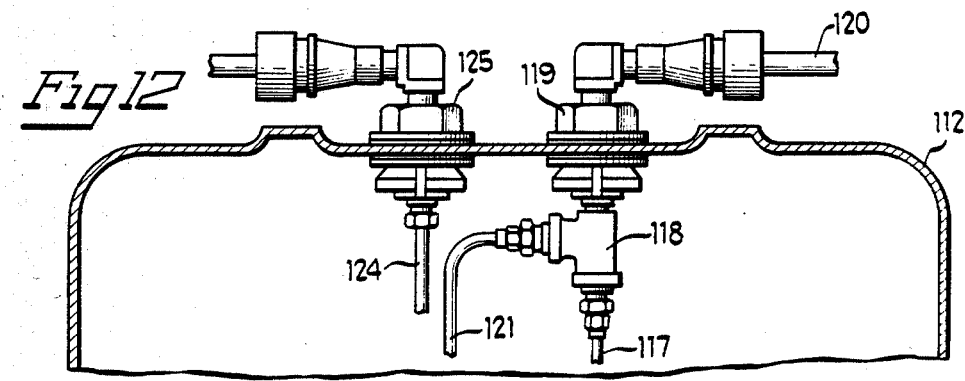

ULTRASONIC NONDESTRUCTIVE TUBING INSPECTION SYSTEM

BACKGROUND OF THE INVENTION

The present invention relates to systems for inspecting tubular products, especially products which are subject to tube wall degradation and thinning. In particular, the present invention relates to a system for inspecting the thinned region of tube walls and for determining the extent of "wastage", i.e., the volume of material lost. While the invention may be useful with any type of tubular products, it has particular application to the inspection of the heat exchange tubes of a nuclear steam generator.

A nuclear steam generator contains many vertical tubes aligned in rows and columns in close relationship to each other, and having their lower ends mounted in a tube sheet. A primary fluid, having been heated by circulation through the nuclear reactor core, is circulated through the tubes. At the same time a secondary fluid, known as feedwater, is circulated around the tubes in heat transfer relationship therewith, thereby transferring heat from the primary fluid in the tubes to the secondary fluid surrounding the tubes, causing a portion of the secondary fluid to be converted to steam.

Deposits tend to settle out of the feedwater and build up along the tube sheet forming deposits known as "sludge". This sludge alters the chemistry of the feedwater, causing it to attack the outer surfaces of the tubes, resulting in localized pitting, corrosion loss or cracking. The integrity of the tubes can also be degraded by mechanical stresses which may result in wear scars or the like.

Isolation of the radioactive primary fluid from the secondary fluid in a nuclear steam generator is critical. Accordingly, test procedures have been developed to test the integrity of the generator tubes. One such procedure is an inspection process, wherein a defect-sensing probe is inserted into a tube and retracted from it at a constant rate. In the event that defects are located in the tube, such defects may be corrected by sleeving, i.e., mounting an auxiliary tube inside the defective tube to span the defective region, thereby returning the tube to its normal heat transfer capacity.

Typically, this testing of the tube integrity is accomplished using eddy current techniques, wherein a probe sets up an electromagnetic field which induces eddy currents in the tube wall, which are in turn detected by a sensor in the probe. The nature of the eddy currents is affected by discontinuities in the tube wall. While the eddy current technique is successful for the detection and characterization of many types of tubing degradation, such as cracks, pits, wear, etc., these techniques have not proved reliable for the detection of discontinuities with dimensions less than about 10% of the tubing wall thickness. Consequently, when it is necessary to develop a precision characterization of tubing damage to assess projected performance, eddy current methods are not always adequate. For example, the accurate assessment of tubing erosion or wear, i.e., wall thinning, requires data concerning the volume of material removed from the tube wall. This volume may be significant even though the wear scar is very shallow, if its overall area is sufficiently large. Yet eddy current techniques cannot accurately detect and characterize such shallow wear scars.

SUMMARY OF THE INVENTION

The present invention relates to an improved tubing inspection system which avoids the disadvantages of prior inspection systems while affording additional structural and operating advantages.

It is a general object of the present invention to provide an improved tubing inspection system which is capable of detecting and characterizing tube wall discontinuities with relatively small dimensions, including those with dimensions less than about 10% of the tube wall thickness.

Another important object of this invention is the provision of an inspection system for detecting tube thinning which utilizes ultrasonic techniques.

Yet another object of this invention is the provision of a system of the type set forth which generates data sufficient to determine the volume of material removed from the tube wall.

In connection with the foregoing object, it is another object of this invention to provide a system of the type set forth, which generates a three-dimensional contour map of the wall thinning.

It is another object of the invention to provide an improved system of the type set forth, which provides for accurate positioning and movement of an ultrasonic probe in the tube being tested.

These and other objects of the invention are attained by providing a system for determination of the extent of erosion in a degraded area of the wall of a heat exchange tube of a nuclear steam generator, the system comprising: ultrasonic means including transducer means and control means, the transducer means being responsive to the control means for emitting ultrasonic waves and receiving reflected waves generally parallel to an emission axis, drive means coupled to the transducer means for moving it axially and rotatably inside a tube along an inspection region with the emission axis disposed radially of the tube so that the emission axis describes a helical path along the tube wall, the control means being responsive to reflected ultrasonic waves from the inner and outer surfaces of the tube wall for producing a thickness signal indicative of the thickness of the tube wall, means for producing position signals respectively indicative of the axial and angular position of the transducer means within the tube, and processing means responsive to the thickness signal and to the position signals for producing a plot of the tube wall thickness around the entire circumference thereof along a predetermined axial extent thereof, thereby to provide a map of the tube wall thickness in the degraded area.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 5 is a fragmentary, partially exploded view in front elevation of the probe positioning apparatus of FIG. 4, with the housing cover removed;

FIG. 6 is a top plan view of the probe positioning apparatus of FIG. 5, rotated 90° counterclockwise;

FIG. 7 is a fragmentary side elevational view of the probe positioning apparatus of FIG. 6, as viewed from the lower side thereof, and with a portion of the housing broken away;

FIG. 8 is a rear elevational view of the probe positioning apparatus of FIG. 5;

FIG. 9 is an enlarged side elevational view of the probe assembly of the present invention;

FIG. 10 is a top plan view of the coupling fluid apparatus of the present invention;

FIG. 11 is an enlarged, fragmentary sectional view of the apparatus of FIG. 10, taken along the line 11—11 therein;

FIG. 12 is an enlarged, fragmentary sectional view of the apparatus of FIG. 10, taken along the line 12—12 therein;

DESCRIPTION OF THE PREFERRED EMBODIMENT

Figure 1:
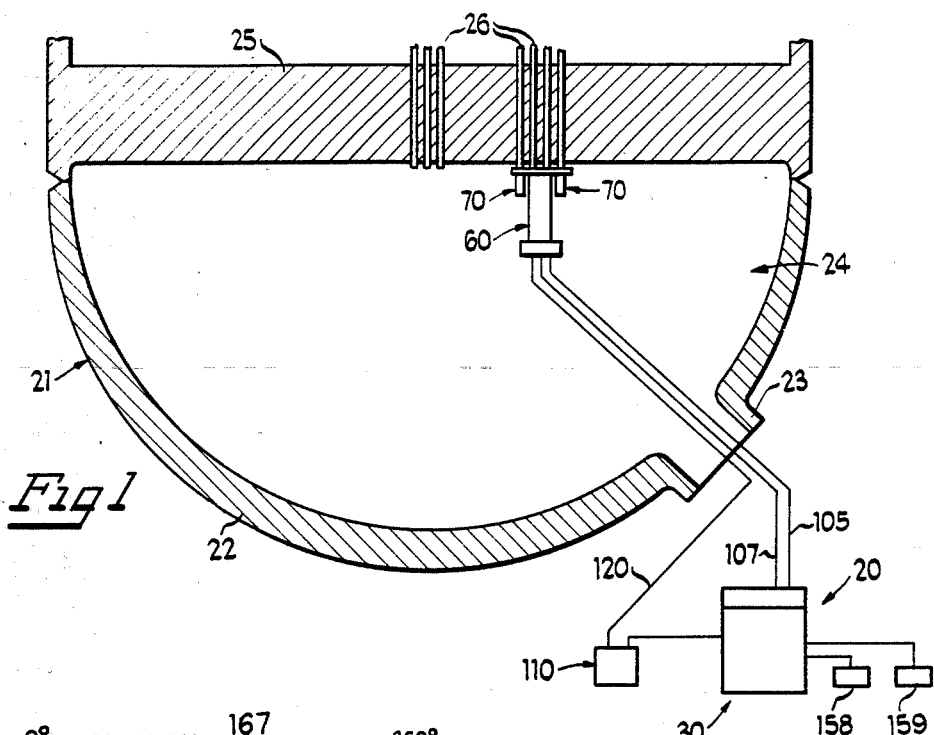
FIG. 1 is a fragmentary, sectional view of the lower end of a nuclear steam generator vessel, diagrammatically illustrating the inspection system of the present invention.
Figure 2:
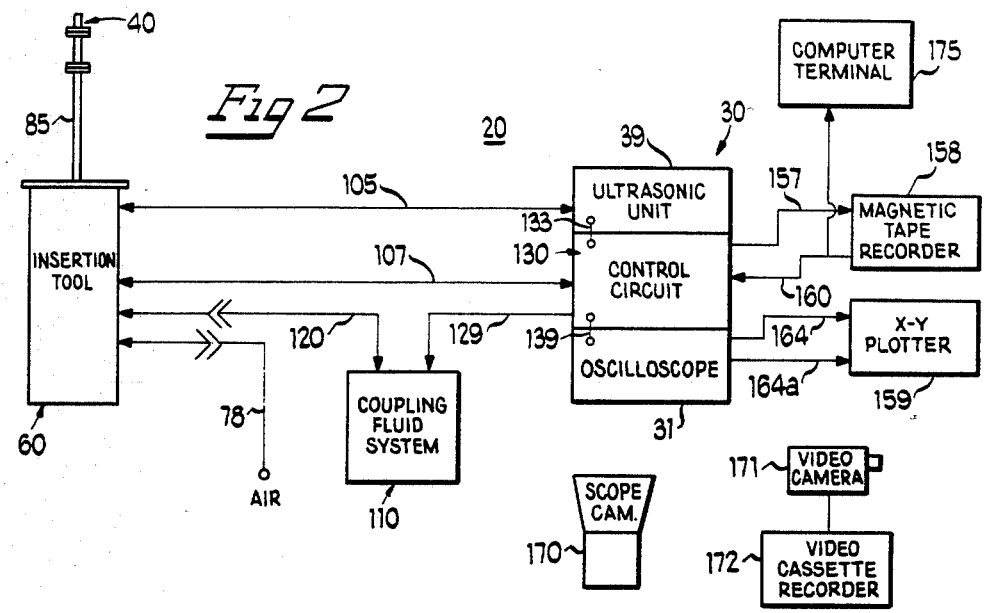
FIG. 2 is a block diagram of the inspection system of the present invention.
Figure 3:
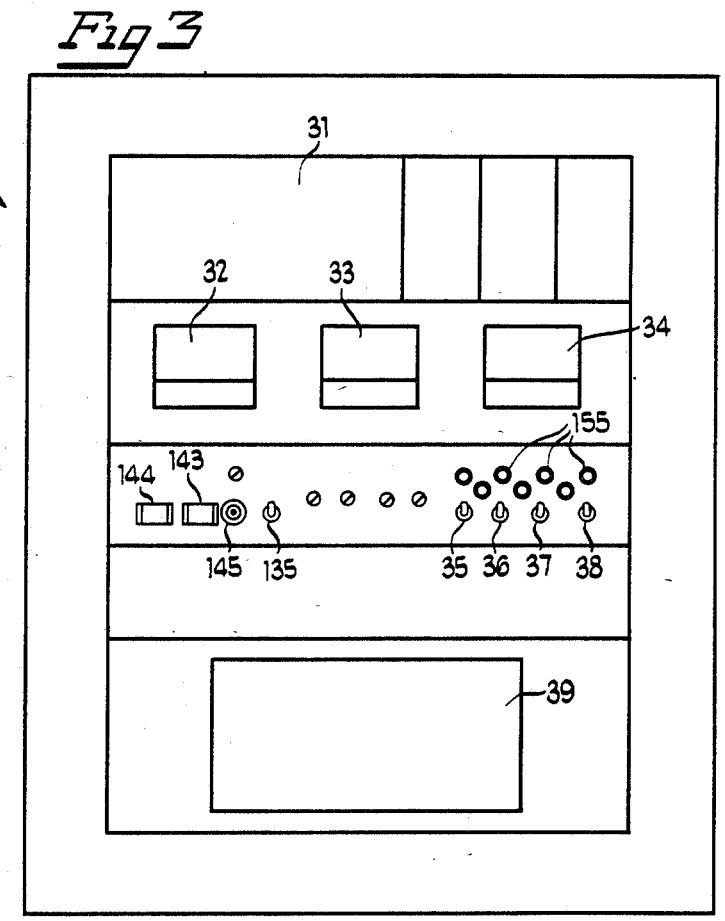
FIG. 3 is an enlarged front elevational view of the control box of the present invention.

Referring to FIGS. 1-3 of the drawings, there is illustrated an inspection system, generally designated by the numeral 20, constructed in accordance with and embodying the features of the present invention. The inspection system 20 is particularly designed for use with a nuclear steam generating plant. More specifically, referring to FIG. 1, such a steam generating plant includes a steam generator vessel 21 having a vessel wall 22 with a part-spherical lower end, provided with one or more manways 23 (one shown) for providing access to an interior primary chamber 24. Overlying and closing the primary chamber 24 is a circular tube sheet 25 having a plurality of vertical bores therethrough in which are respectively received the lower ends of a plurality of heat exchange tubes 26, only representative ones of which are shown. Each of the tubes 26 may be of an inverted U-shape and projects upwardly well above the tube sheet 25 in heat exchange relationship with the surrounding feedwater, all in a well known manner.

Figure 4:
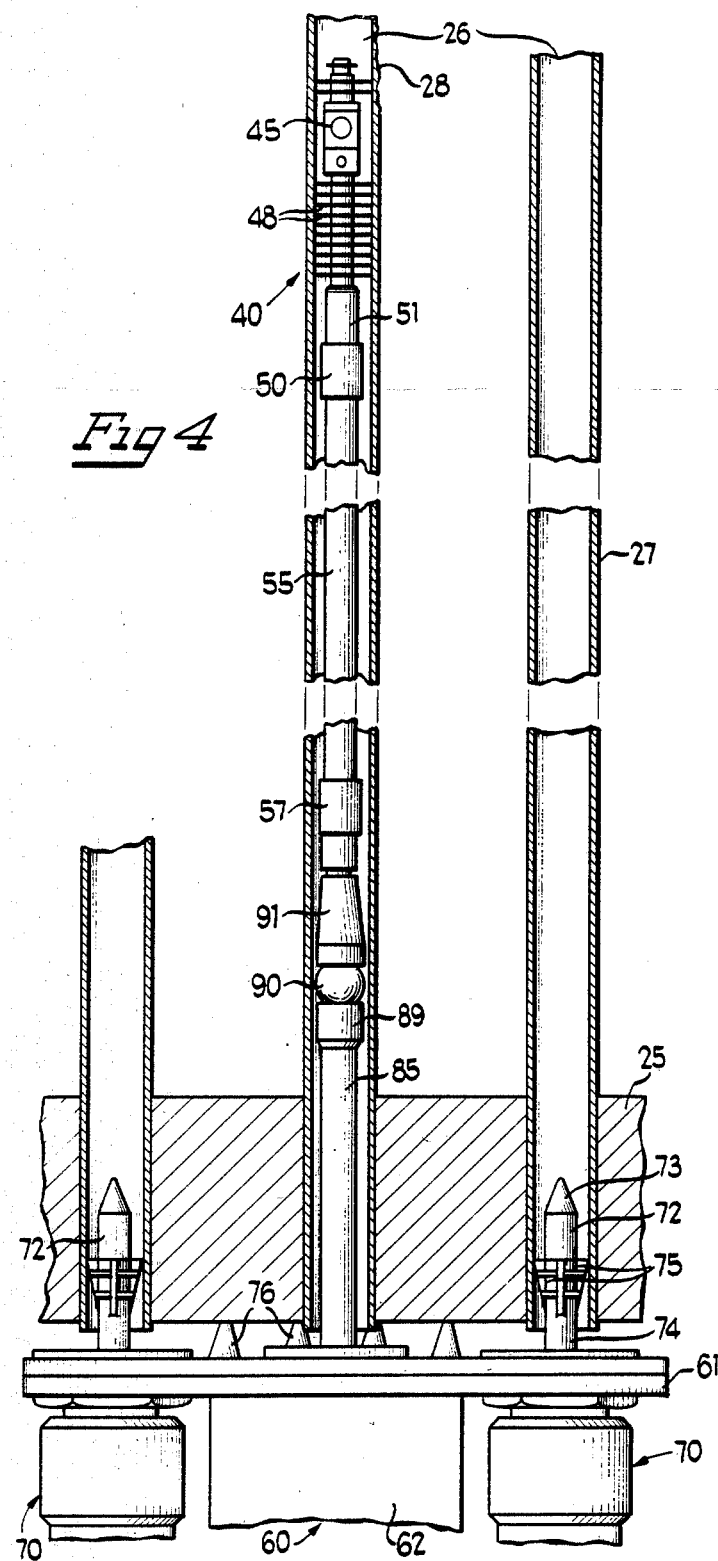
FIG. 4 is an enlarged, fragmentary view in partial vertical section, illustrating the manner of mounting and use of the probe positioning apparatus of the present invention.

Each of the tubes 26 has a cylindrical tube wall 27 (see FIG. 4). As is well understood in the art, in use the outer surfaces of the tube walls 27 may develop areas 28 of wall loss or wear scars and other types of degradation which result in thinning of the tube wall 27 and can jeopardize the tube integrity. The inspection system 20 is a system for inspecting each of the tubes 26 to determine the extent of such tube wall loss.

Generally, referring to FIG. 2, the inspection system 20 includes a control box 30 which is coupled to an insertion tool 60 for driving an ultrasonic probe assembly 40 axially into an associated one of the tubes 26. The control box 30 includes an ultrasonic thickness measuring unit 39 which is coupled by a cable 105 to the insertion tool 60 for transmitting drive pulses to the probe assembly 40 and receiving signals therefrom relative to the thickness of the tube wall 27. The control box 30 also includes a control and data handling circuit 130 which is coupled by a cable 107 to the insertion tool 60 for transmitting drive power thereto and for receiving therefrom signals relative to the axial and angular position of the probe assembly 40. The control and data handling circuit 130 operates on the position signals and on the thickness signals from the ultrasonic thickness measuring unit 39 to produce on an oscilloscope 31 a display mapping the thickness of an inspection region of the tube wall 27.

An air conduit 78 couples the insertion tool 60 to an associated source of pressurized air for operation of associated cam lock assemblies to be explained below. A coupling liquid is inserted into the tube 26 through the probe assembly 40 from a coupling fluid system 110 via a conduit 120, the coupling fluid system 110 being controlled by the control and data handling circuit 130 via a cable 129. Data from the probe assembly 40 and the insertion tool 60 may be temporarily stored in a magnetic tape recorder 158, and the signals displayed on the oscilloscope 31 may also be output to an X-Y plotter 159. In order to record the displays on the oscilloscope 31 and the ultrasonic thickness measuring unit 39, there may also be provided a scope camera 170 and/or a video camera 171 and associated video cassette recorder 172 (see FIG. 2).

The inspection system 20 includes a control box 30 which contains a number of components of control and display equipment. Referring to FIGS. 2 and 3, the control box 30 includes a storage oscilloscope 31 and a plurality of meters 32, 33 and 34, which may be ammeters and are used for monitoring control currents, as will be explained more fully below. A number of control switches, 35, 36, 37, 38 and 135 are also provided on the front panel of the control box 30 to control various operations of the system 20, as will be explained below. Mounted in the lower portion of the control box 30 (diagrammatically shown at the top in FIG. 2) is an ultrasonic thickness measuring unit 39, which may be of the type sold under the trademark "NOVASCOPE", Model No. 2000, by NDT Instrument Inc. The operation of the thickness measuring unit 39 will be explained more fully below.

Referring now also to FIGS. 4, 5 and 9, there is associated with the thickness measuring unit 39 a probe assembly, generally designated by the numeral 40. The probe assembly 40 includes an elongated tubular member 41 (FIG. 9) having an enlarged-diameter portion 42 provided with a radially extending outlet orifice 43. Formed in one side of the enlarged-diameter portion 42 is a notch 44 for receiving an ultrasonic transducer 45 which generates ultrasonic waves and emits them generally radially through an aperture 46. Surrounding the tubular member 41, except for the enlarged-diameter portion 42 thereof, are a plurality of axially spaced-apart alternating spacers 47 and centering rings 48.

Figure 14:
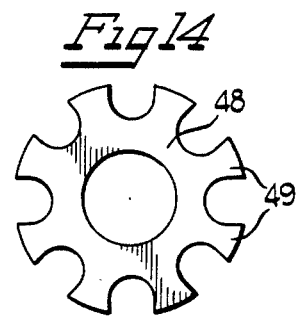
FIG. 14 is a plan view of one of the centering rings of the probe assembly of FIG. 9.

The centering rings 48 are preferably in the form of rosettes with radially extending flexible tines 49 (see FIG. 14), the maximum outer diameter of the centering rings 48 preferably being substantially equal to the inner diameter of the associated tubes 26. Thus, when the probe assembly 40 is inserted axially into a tube 26, the centering rings 48 will flexibly and slidably engage the inner surface of the tube wall 27 and maintain the probe assembly 40 in a position substantially coaxial with the tube 26, as is best illustrated in FIG. 4. Preferably, the diameter of the enlarged diameter portion 42 is slightly less than the inner diameter of the tube 26.

The lower end of the tubular member 41 is coupled to an adapter 50 (FIGS. 4 and 5). More specifically, the adapter 50 has a female end 51 which threadedly receives a male coupling 52 (FIG. 9) on the lower end of the tubular member 41. The lower end of the adapter 50 is provided with a male end 53 (FIG. 5) which is adapted to be received in and coupled to one end of an associated flexible hollow drive shaft 55, the other end of which receives a male coupling 56 on an adapter 57. It will be appreciated that, if necessary, several sections of the flexible drive shaft 55 can be interconnected by the use of suitable coupling adapters to provide a shaft of any desired length. Extending through the flexible drive shaft 55 and the tubular member 41 of the probe assembly 40 is an elongated electrical cable 54, one end of which is coupled to the transducer 45. Preferably, the cable 54 is provided with connectors 59 (FIG. 5) so that sections of cable 54 can be joined together, as desired, to produce a cable of any desired length. The cable 54 transmits signals to and from the transducer 45, as will be explained more fully hereinafter. The adapter 57 is provided with an externally threaded male coupling 58 at its lower end.

The probe assembly 40 and its associated flexible drive shaft 55 are adapted to be coupled to the insertion tool 60. Referring in particular to FIGS. 4-8, the insertion tool 60 has a flat, generally triangular base plate 61 to which is fixedly secured a box-like housing 62. The housing 62 includes a rear wall 63, a front wall 64, side walls 65 and 66 and a bottom wall 67, the upper end of the housing 62 being closed by the base plate 61. A handle 68 is secured by mounting brackets 69 to the rear wall 63 to facilitate manipulation of the insertion tool 60.

Mounted on and depending from the base plate 61, as respectively at opposite ends thereof, are two cam lock semblies, each generally designated by the numeral 70. Each of the cam lock assemblies 70 includes a pneumatic cylinder 71 provided with a piston rod or plunger 72 which extends upwardly through an associated opening in the base plate 61. The plunger 72 has a diameter substantially less than the inner diameter of the tubes 26 and has a conical tip 73 to facilitate insertion into a tube 26. Surrounding the plunger 72 is an expansion sleeve 74 provided with radially pivotable fingers 75. As the plunger 72 is moved upwardly through the expansion sleeve 74, it spreads the finger 75 and moves them into frictional engagement with the inner surface of an associated tube 26 (see FIG. 4).

Thus, in use, the two cam lock assemblies 70 are disposed with the expansion sleeves 74 thereof respectively received in two of the tubes 26, firmly to anchor the insertion tool 60 against the lower side of the tube sheet 25. Spacer lugs 76 are provided on the base plate 61 to engage the lower surface of the tube sheet 75 and position the insertion tool 60 at the proper distance therefrom. It will be appreciated that the insertion tool 60 is tailored to a particular tube pitch array for a particular type of nuclear steam generator. This arrangement is such that when the cam lock assemblies 70 are mounted in position, as illustrated in FIG. 4, the insertion tool 60 will be oriented for inserting the probe assembly 40 into an intermediate one of the tubes 26, as will be explained below. For a different tube pitch array, a different insertion tool arrangement with differently-spaced cam lock assemblies 70 would be used. It will be appreciated that the cam lock assemblies 70 are coupled to an associated source of pressurized air through the conduit 78 (see FIGS. 2 and 7).

The insertion tool 60 includes a drive assembly, generally designated by the numeral 80. The drive assembly 80 includes a reversible gearmotor 81 provided with a pinion 82 on its output shaft disposed in meshing engagement with an axially elongated spur gear 83. The spur gear 83 is, in turn, disposed in meshing engagement with a travel gear 84 which is fixed on an elongated hollow tubular shaft 85. The shaft 85 is journaled in a bearing 86 with shaft seal secured to the base plate 61 and extends upwardly through a complementary opening in the base plate 61. A portion of the shaft 85 beneath the travel gear 84 is externally threaded and is disposed in threaded engagement with an internally threaded bushing 87 which is spaced several inches beneath the base plate 61 and is fixedly secured to the housing 62.

In operation, rotation of the gearmotor 81 effects a corresponding rotation of the spur gear 83, which in turn rotates the shaft 85 via the travel gear 84. Because of the threaded engagement with the fixed bushing 87, as the shaft 85 rotates it is axially advanced or retracted relative to the bushing 87. The axial elongation of the spur gear 83 is sufficient to maintain threaded engagement with the travel gear 84 during the entire range of axial movement of the shaft 85, which is limited by the spacing between the base plate 61 and the bushing 87. Preferably, limit switches (not shown) are provided for de-energizing the gearmotor 81 just before the shaft 85 reaches the extremities of its axial travel, to prevent damaging engagement of the travel gear 84 with the base plate 61 or the bushing 87.

The upper end of the shaft 85 is provided with a coupling 89 for mounting a flexible resilient hollow seal 90, which has an outer diameter slightly greater than the inner diameter of the associated tube 26. The seal 90 is in turn coupled to a hollow female adapter 91 which is internally threaded for threaded engagement with the male coupling 58 of the adapter 57 to connect the lower end of the flexible drive shaft 55 to the shaft 85. Thus, it will be appreciated that axial and rotational movement of the shaft 85 will effect a corresponding axial and rotational movement of the flexible drive shaft 55 and the probe assembly 40.

The spur gear 83 is also disposed in meshing engagement with a gear 92 fixed to the shaft of a rotary encoder 93 (FIGS. 5 and 7), which may be a potentiometer. Thus, it will be appreciated that the encoder 93 will generate a signal indicative of the angular position of the shaft 85 and, thus, the angular position of the transducer 45. The insertion tool 60 also includes a linear encoder 94 (FIG. 7), which may also be a potentiometer having a slider (not shown) fixedly secured to a bracket 106 carried by the shaft 85. Thus, as the shaft 85 is moved axially, the slider is moved so that the encoder 94 produces a signal indicative of the axial position of the shaft 85 and the transducer 45. The signals from the encoders 93 and 94 are fed through the cable 107 via conductors 108 and 109, respectively, (see FIGS. 13A and B) to the control and data handling circuit 130, in a manner which will be described more fully below.

Fixedly secured to and surrounding the shaft 85 beneath the bushing 87 is a jacket 95, provided with suitable O-ring seals (not shown). The jacket 95 is coupled by a suitable conduit (not shown) to a fitting 96 extending through the rear wall 63, the fitting 96 being in turn coupled to the conduit 120 for transmitting coupling fluid to and from the coupling fluid apparatus 110. The portion of the shaft 85 within the jacket 95 has an aperture (not shown) for introducing the coupling fluid into the interior of the hollow tubular shaft 85. This conduit has sufficient length to accommodate the axial movement of the shaft 85.

Each of the cam lock assemblies 70 is coupled by suitable pneumatic conduits (see FIG. 8) through fittings in the rear wall 63 to conduits 97 (FIGS. 5 and 7), which are in turn coupled to a control valve 98. The control valve 98 is in turn coupled to a valve 99 which is connected through a suitable fitting to the conduit 78 (FIGS. 2 and 7) which leads to the source of pressurized air. The control valve 98 is provided with a toggle switch 98a (FIG. 8) mounted on the rear wall 63 for selectively controlling which of the conduits 97 is provided with air. When one of the conduits 97 is supplied with air, the air is provided to the lower ends of the cylinders 71 for extending the plungers 72, while when the other conduit 97 is supplied with air, air is provided to the tops of the cylinder 71 for retracting the plungers 72.

The lower end of the shaft 85 is coupled through a suitable adapter 100 and receptacle 101 to a slip ring 102 which maintains electrical contact with the cable 54 during rotation of the shaft 85. The slip ring 102 is coupled to a connector 103 carried by a bracket 104 which is mounted on the bracket 106 and movable therewith. The connector 103 is connected by a section of coaxial cable 104a (FIG. 7) to a receptacle fitting 104b (FIGS. 5 and 8) in the rear wall 63, which is in turn coupled to the cable 105 leading to the control box 30. The cable section 104a is terminated with a matching impedance 105a (FIG. 5). Thus, it will be appreciated that signals are communicated between the ultrasonic thickness measuring unit 39 and the probe assembly 40 via the coaxial cable 105, the cable section 104a, the slip ring 102 and the cable 54.

Referring now also to FIGS. 10–12 of the drawings, the coupling fluid apparatus 110 includes a box-like housing 111 provided with a removable cover 112, and in which is disposed a reservoir container 113, which may be in the form of a plastic bottle or the like. The container 113 is provided at its upper end with an access opening in which is received a fitting 114 accommodating three conduits. A conduit 115 extends from adjacent to the bottom of the container 113, through the fitting 114 and to the inlet port of a pump 116 which is driven by an electric pump motor 116a. The outlet port of the pump 116 is coupled by a conduit 117 to a tee 118, which is in turn coupled through a fitting 119 in the cover 112 to the conduit 120 leading to the insertion tool 60. Preferably, the pump 116 is a one-way pump, being provided with suitable valve means to prevent backflow therethrough.

Another conduit 121 extends from the tee 118 to the inlet port of a solenoid-actuated valve 122, the outlet port of which is coupled to a conduit 123 which extends through the fitting 114 to the bottom of the container 113. Another conduit 124 extends from the fitting 114 to a vent fitting 125 in the cover 112 for venting the container 113 to atmosphere. Also mounted in the cover 112 is an electrical connector 126, through which are coupled conductors 127 for energizing the valve 122 and conductors 128 for energizing the pump motor 116a. The conductors 127 and 128 form part of a cable 129 which extends between the coupling fluid apparatus 110 and the control circuit and data handling 130 of the control box 30.

In operation, when it is desired to deliver coupling fluid to the insertion tool 60, the valve 122 is closed and the pump 116 is actuated to pump fluid from the container 113 to the insertion tool 60. During ultrasonic inspection the pump 116 is deactuated and the valve 122 remains closed. To recover the coupling fluid, the valve 122 is opened, allowing the coupling fluid to flow by gravity back to the container 113.

Figure 13H:
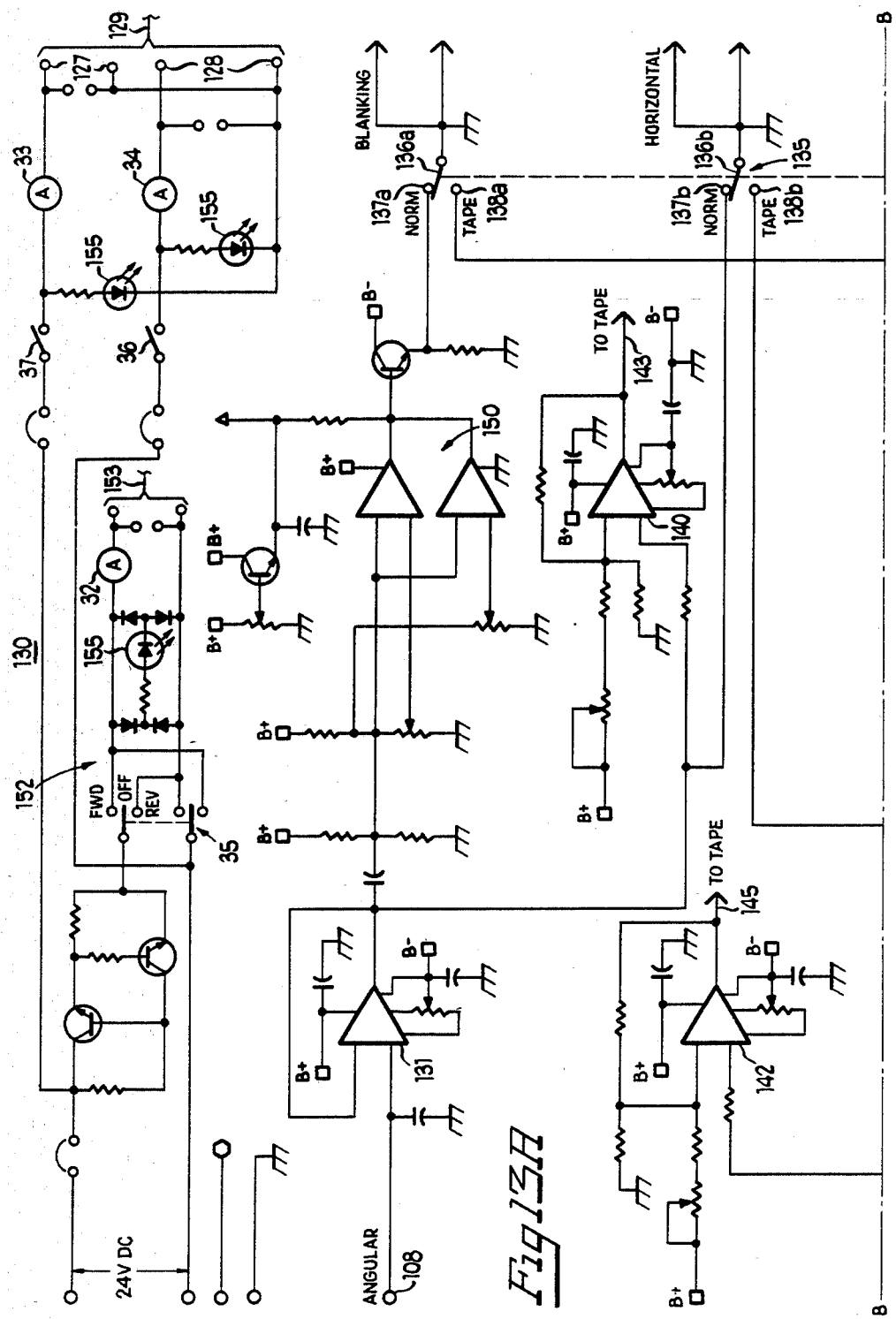
FIGS. 13A and 13B are a schematic electrical circuit diagram of the control and data handling circuit of the present invention.
Figure 13B:
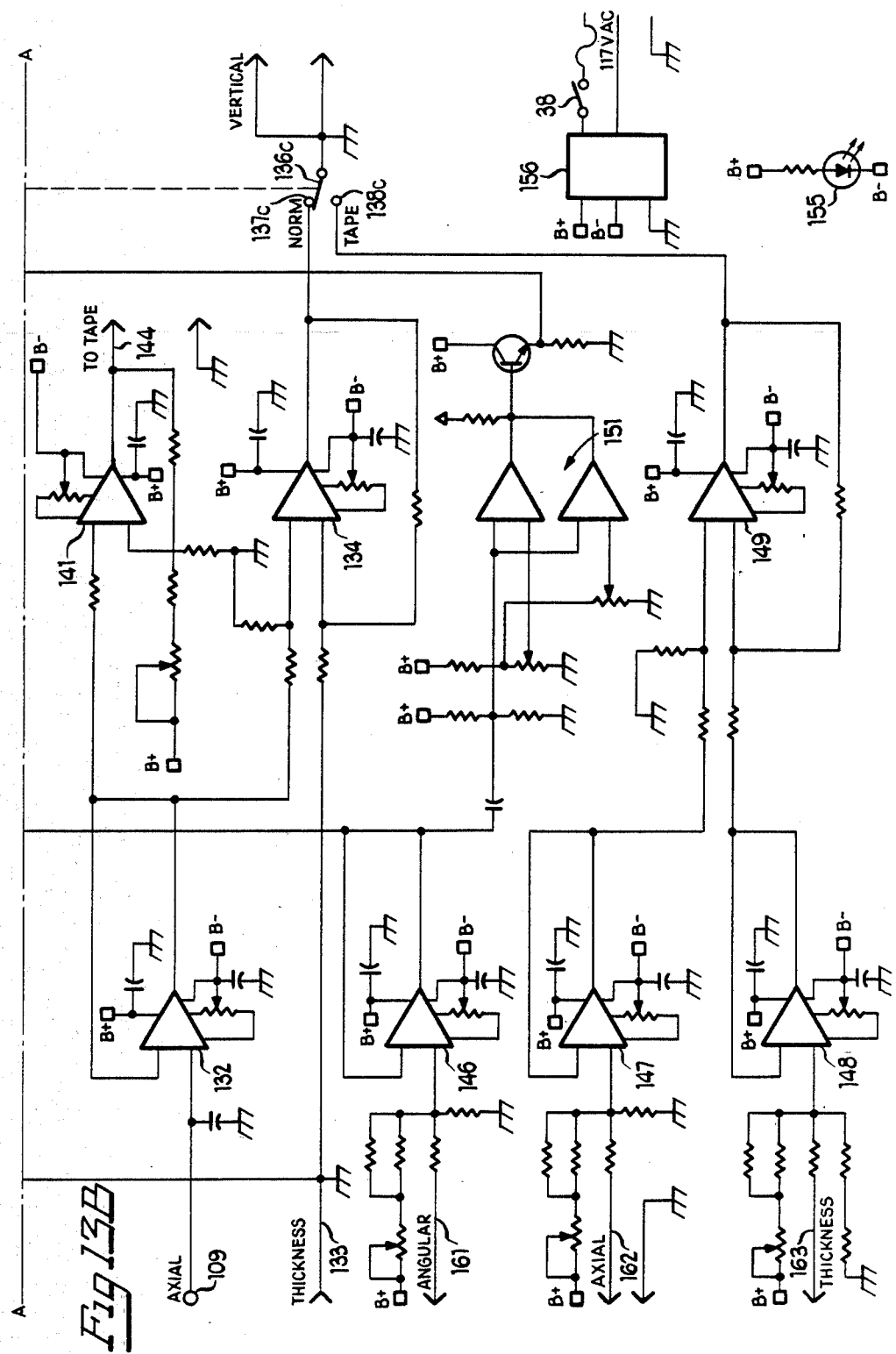

Referring now also to FIGS. 13A and B, the control and data handling circuit 130 will be described. In order to read the circuit diagram FIG. 13A should be placed immediately above FIG. 13B. The control and data handling circuit 130 includes buffer amplifiers 131 and 132, each of which is preferably in the form of a unitary gain operational amplifier circuit, having the inputs thereof respectively connected to the conductors 108 and 109 which extend, respectively, from the outputs of the rotary encoder 93 and the linear encoder 94 in the insertion tool 60. A thickness indicating signal from the ultrasonic thickness measuring unit 39 is supplied by a conductor 133 to a gain-of-two input of an operational amplifier summer 134, the other input of which is connected to the output of the buffer amplifier 132. The output of the summer 134 is applied to one of the fixed contacts of one pole "c" of a three-pole, double-throw selector switch 135 having poles "a", "b" and "c". More specifically, the selector switch 135 has a set of movable contacts 136a, 136b and 136c, a first set of fixed contacts 137a, 137b and 137c and a second set of fixed contacts 138a, 138b and 138c. In normal operation, the movable contacts 136a–c are in contact with the fixed contacts 137a–c, respectively.

The movable contacts 136a–c are also respectively connected to conductors of a cable 139 (see FIG. 2) which extends from the control and data handling circuit 130 to the oscilloscope 31 of the control box 30. More specifically, the movable contact 136a is connected to the retrace blanking circuit of the oscilloscope 31 and the movable contacts 136b and 136c are respectively connected to the horizontal and vertical inputs of the oscilloscope 31. The fixed contact 137a is connected to the output of a blanking circuit 150 comprising two operational amplifiers, the inputs of which are connected to the output of the buffer amplifier 131, which is also connected to the fixed contact 137b.

Thus, it will be appreciated that when the selector switch 135 is in the normal position illustrated in FIGS. 13a and b, the signal from the rotary encoder 93, which corresponds to the horizontal position of the transducer 45, is fed to the horizontal input of the oscilloscope 31 via the buffer amplifier 131 and pole "b" of switch 135. The blanking circuit 150 operates on the angular position signals from the rotary encoder 93, which are in the form of a sawtooth voltage, to produce blanking pulses which are applied to the oscilloscope 31 via pole "a" of switch 135 to eliminate retrace in the oscilloscope display. The signal from the linear encoder 94, which corresponds to the axial or vertical position of the transducer 45, is first added in the summer 134 to twice the thickness signal from the ultrasonic thickness measuring unit 39, and this sum is applied to the vertical input of the oscilloscope 31 via pole "c" of switch 35.

The position and thickness signals are also simultaneously stored in the magnetic tape record 158, for later use. Thus, the outputs of the buffer amplifiers 131 and 132 and the thickness signal on the conductor 133 are respectively applied to the inputs of operational amplifier circuits 140, 141 and 142, the output terminals 143, 144 and 145 of which are respectively coupled to the input of the magnetic tape recorder 158 via the cable 157 (see FIG. 2).

It is a significant aspect of the present invention that the display on the oscilloscope 31 can be derived from the signals stored on the tape recorder 158, rather than from signals received directly from the insertion tool 60 and the ultrasonic thickness measuring unit 39. In this case, the selector switch 135 is switched so that the movable contacts 136a–c thereof are in contact, respectively, with the fixed contacts 138a–c. The contact 138c is connected to the output of an operational amplifier summer 149, the inputs of which are respectively connected to the outputs of operational amplifier circuits 147 and 148, the latter input being a gain-of-two input. The contact 138b is connected to the output of an operational amplifier circuit 146. The contact 138a is connected to the output of a blanking circuit 151, the input of which is coupled to the output of the operational amplifier circuit 146. The inputs of the operational amplifier circuits 146, 147 and 148 are respectively connected via conductors 161, 162 and 163 to outputs from the tape recorder 158, which respectively carry the angular and axial position signals and the thickness signal. The conductors 161, 162 and 163 form part of the cable 160 extending between the tape recorder 158 and the control and data handling circuit 130 (see FIG. 2). The horizontal and vertical signals which are transmitted to the oscilloscope 31, may also be transmitted to the X-Y plotter 159 by the conductors 164 and 164a (see FIG. 2).

The control and data handling circuit 130 also includes a motor control circuit 152 which has output terminals 153 for applying power via the cable 107 to the gearmotor 81 of the drive assembly 80 in the insertion tool 60. The motor control circuit 152 includes the double-pole, double-throw switch 35, which is mounted on the front panel of the control box 30 (see FIG. 3). The switch 35 is biased to a normal OFF position and is movable up and down, respectively, to FORWARD and REVERSE positions for controlling the direction of rotation of the gearmotor 81 for insertion and retraction of the probe assembly 40.

The control circuit 140 also applies power through the single-pole, single-throw switches 36 and 37, respectively to the output terminals 127 and 128, for respectively controlling the solenoid valve 122 and the pump motor 116a of the coupling fluid apparatus 110, via the cable 129. The ammeters 32, 33 and 34 are respectively connected in series with the output terminals 153, 127 and 128 for indicating the current flow to the gearmotor 81, the solenoid valve 122 and the pump motor 116a. Similarly, LED's 155 are connected in each of these drive circuits for giving a visual indication when the circuits are energized. The B+ and B− supplies for the operational amplifiers of the control and data handling circuit 130 are provided by a power supply circuit 158 which is connected through an on-off power switch 38 to a 117 VAC line, an LED 155 being connected across the output terminals of the power supply 156 to provide a power-ON indication. Preferably, the power supply 156 also provides 24 VDC to the input of the motor control circuit 152.

Figure 15:
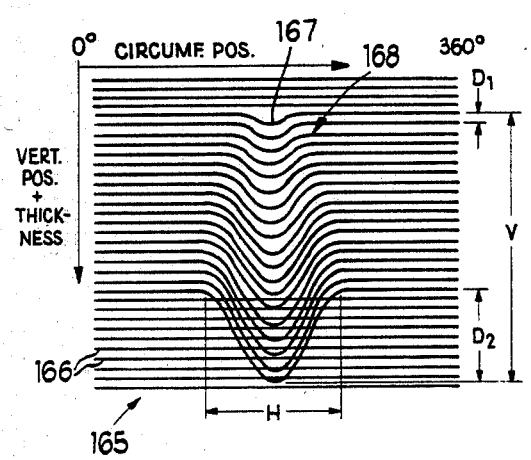
FIG. 15 is a two-dimensional wear map of a section of tube wall, as generated by the circuitry of FIGS. 13A and B, and as displayed on the storage oscilloscope of the control box.

Referring now also to FIG. 15 of the drawings, the operation of the inspection system 20 will be described. FIG. 15 is a plot of a wear map as depicted on the oscilloscope 31 after inspection of an inspection region of a tube 26 by the inspection system 20. The insertion tool 60 and the associated probe assembly 40 are carried inside the primary chamber 24 of the steam generator vessel 21 by an operator through a manway 23. The remainder of the inspection system 20 is located outside the steam generator vessel 21, as in an associated control trailer, being connected to the insertion tool 60 by the cabling illustrated in FIG. 20.

Typically, areas of possible wall loss will have been previously located by other inspection techniques. For a given tube 26, a sufficient length of flexible drive shaft 55 will be selected to reach a predetermined inspection region in the vicinity of one of the possible wall loss sites. When the proper length of flexible drive shaft 55 has been connected to the shaft 85, and the probe assembly 40 has been mounted on the distal end of the flexible drive shaft 55, the probe assembly 40 is inserted into the selected tube 26 and manually pushed up into the tube 26 until the full length thereof has been received in the tube 26. The insertion tool 60 is then manually lifted up into position for inserting the upper end of the shaft 85 into the selected tube 26, the insertion tool 60 being oriented so that the upper end of the cam lock expansion sleeves 74 are respectively received in adjacent tubes 26 until the spacer lugs 76 bear against the bottom surface of the tube sheet 25, as illustrated in FIG. 4. The toggle switch 98a on the insertion tool housing 62 is then operated to supply pressurized air to the lower ends of the cam lock cylinders 71, extending the plungers 72 to expand the fingers 75 and frictionally lock the insertion tool 60 in place against the tube sheet 25 in a known manner.

It will be appreciated that as the probe assembly 40 is inserted into the tube 26, the centering rings 48 slidably resiliently engage the inner surface of the tube 26 to maintain the transducer 45 centered in the tube 26. Similarly, the seal 90 slidably and resiliently engages the inner surface of the tube 26 around the entire circumference thereof to provide a movable, yet fluid-tight seal. When the probe assembly 40 is thus inserted in the tube 26, the transducer 45 will be oriented so as to emit ultrasonic waves through the aperture 46 and to receive reflected waves substantially parallel to an emission axis which is disposed substantially radially of the tube 26. When the insertion tool 60 has been thus mounted in place, the operator leaves the steam generator vessel 21, and the remainder of the inspection operation is controlled remotely from the control box 30.

The remote operator first throws the ON-OFF switch 38 on the control box 30 to energize the power supply 156 for the control and data handling circuit 130. He then closes the switches 36 and 37 for supplying coupling fluid to the tube 26. The coupling fluid, which is typically water, with or without a wetting agent, is necessary to provide a transmission medium for the ultrasonic waves, since ultrasonic waves couple much more readily and with much lower loss with a water medium than with air. The closure of the switch 37 actuates the solenoid valve 122 for closing it, and closure of the switch 36 energizes the pump motor 116a for actuating the pump 116. Thus, the coupling fluid is pumped from the reservoir container 113 to the insertion tool 60 via the conduit 115, the pump 116, the conduit 117, the tee 118, the fitting 119, the conduit 120 and the fitting 96. The fluid then travels through a conduit (not shown) in the insertion tool housing 62 to the jacket 95 around the shaft 85. The fluid then flows through the associated opening in the shaft 85 and thence upwardly through the shaft 85, the flexible drive shaft 55 and the tubular member 41 of the probe assembly 40, being emitted into the tube 26 through the outlet orifice 43 in the tubular member 41. Sufficient coupling fluid is pumped into the tube 26 to fill it from the seal 90 to above the region of the expected wear scar 28. When the tube 26 has been filled to a sufficient level, the pump motor 116a may be turned off. The one-way nature of the pump 116, together with the closed solenoid valve 122, prevents retrograde flow of coupling fluid back to the container 113.

Next, in the disclosed embodiment, the operator moves the selector switch 35 upwardly to the FORWARD position for energizing the gearmotor 81 to advance the shaft 85 into the tube 26 until the shaft 85 has been fully extended. Preferably, the length of flexible drive shaft 55 has been selected so that, when the insertion tool 60 has been locked in place as illustrated in FIG. 4, the flexible drive shaft 55 is fully extended in the tube 26, and the shaft 85 has been extended, the transducer 45 will be located at the upper end of the inspection region, just above the site of the possible wall loss 28.

If it is desired to obtain a direct real-time read-out of the inspection measurements, the selector switch 135 is placed in the normal position illustrated in FIGS. 13A and B for passing the position and thickness signals directly to the oscilloscope 31 and, if desired, to the X-Y plotter 159. The ultrasonic thickness measuring unit 39 is then energized for transmitting high-voltage pulses over the cable 105 to the insertion tool 60, and thence via the cables 104a and 54 to the transducer 45 in the probe assembly 40. These pulses cause the transducer 45 to emit ultrasonic waves of a predetermined power and frequency and direct them radially to the tube wall 27.

The ultrasonic signals are reflected from the inner and outer surfaces of the tube wall 27, returned to the transducer 45 and converted to electrical signals which are transmitted along the cables 54, 104a and 105 to the ultrasonic thickness measuring unit 39. The two reflected signals from the inner and outer surfaces of the tube wall 27 are spaced apart in time by a period proportional to the thickness of the tube wall 27. The ultrasonic thickness measuring unit 39 includes a receiver circuit which converts the difference in time between the two reflected signals to a voltage level indicative of tube wall thickness, which voltage level is output on the conductor 133 (see FIGS. 2 and 13B) to the control and data handling circuit 130.

Next to begin the inspection scan, the operator moves the selector switch down to the REVERSE position for energizing the gearmotor 81 to retract the shaft 85 into the insertion tool 60. Because the shaft 85 is rotating as it retracts, in a screw-type fashion, the ultrasonic waves emitted from the transducer 45 describe a downwardly spiraling helical path along the tube wall 27. Preferably, the inspection system 20 is calibrated so that, at the beginning of the inspection scan, the rotary and linear encoders 93 and 94 are at positions corresponding to the upper left-hand corner of the plot of FIG. 15 representing zero angular and axial displacement. In this regard, it will be noted that in FIG. 15 the horizontal axis represents angular or circumferential displacement and the vertical axis represents axial or vertical displacement plus tube wall thickness, with the upper part of the graph being toward the top of the tube 26 and the lower part of the graph being toward the bottom of the tube 26.

The axial and angular position signals from the rotary and linear encoders 93 and 94 are fed over the cable 107 to the control and data handling circuit 130. The angular position signal is applied on the conductor 108 to the input of the operational amplifier 140, the output of which is applied through the pole "a" of the selector switch 135 to the horizontal input of the oscilloscope 31. The output of the buffer amplifier 131 is also applied to both operational amplifiers of the blanking circuit 150, which produces an output blanking signal, which is applied through the pole "a" of the selector switch 135 to the blanking input of the oscilloscope 31. The blanking circuit 130 generates a blanking pulse once during each 360° rotation of the transducer 45 to provide retrace blanking for the oscilloscope 31. The axial position signal is applied on the conductor 109 to the input of the operational amplifier 132, the output of which is fed to one input of the summer 134. To the other input of the summer 134, which has a gain of two, the thickness signal from the thickness measuring unit 39 is applied on the conductor 133. The output from the summer 134, which represents the sum of the axial position signal and two times the thickness signal, is applied via the pole "c" of the selector switch 135 to the vertical input of the oscilloscope 31.

Referring to FIG. 15, the trace on the oscilloscope screen moves from left to right across the upper part of the screen at a level which is representative of the normal undegraded thickness of the tube wall 27. As long as this thickness remains unchanged, the trace will be a series of straight lines, with each line representing one 360° rotation of the transducer 45, and the spacing between lines representing the axial travel of the transducer 45 during that one revolution. While the oscilloscope trace lines 166 have been illustrated as substantially horizontal, for ease of illustration, it will be appreciated that they are actually inclined slightly downwardly from left to right so that the left-hand end of each trace is at the same level as the right-hand end of the preceding trace. The oscilloscope 31 is a storage oscilloscope, so that the traces remain on the screen for a substantial period of time to permit viewing of the entire plot 165.

When the ultrasonic beam encounters a reduced-thickness area of the tube wall 27, the oscilloscope trace undergoes a downward deflection, as indicated at 167, the vertical extent of this deflection being proportional to the amount of thinning, i.e., the depth of the wear scar 28, and the horizontal extent of the deflection being proportional to the circumferential extent of the wear scar 28. Thus, when the transducer 45 has completed its transit of the inspection region, there results on the oscilloscope screen a map 168 of the wear scar 28. By way of example, referring to FIG. 15, the wear scar depicted therein increases in depth and width from the top to the bottom thereof. The upper end of the wear scar has a depth $D_1$, while the lower end has a depth $D_2$, the scar having a maximum circumferential width H and a vertical or axial extent V. The depth of the wear scar is exaggerated because of the doubling of the amplitude of the thickness signal at the input of the summer 134, which permits wall loss to be more easily viewed.

Instead of viewing the data in real time on the oscilloscope 31, data can also be stored on the magnetic tape recorder 158, for later viewing and/or further processing. Thus, it will be noted that the outputs of the buffer amplifiers 131 and 132, and the thickness voltage on the conductor 133 are respectively also applied to operational amplifiers 140, 141 and 142 which amplify and offset the angular and axial position voltages and the thickness voltage so as to be compatible with the input range of the tape recorder 158, typically ±8 volts. The outputs of the operational amplifier circuits 140, 141, and 142 are then applied to the input of the tape recorder 158 over the cable 157.

When it is desired to display the stored data on the oscilloscope 31, the selector switch 135 is moved down to its tape position, wherein the movable contacts 136a–c are respectively in contact with the fixed contacts 138a–c, and the recorder 158 is operated to play back the stored data over the cable 160, which includes conductors 161, 162 and 163, respectively carrying the angular and axial position signals and the thickness signal. These signals are respectively applied to the inputs of the operational amplifier circuits 146, 147 and 148, which are designed to ensure that the voltage levels of the recorded data are the same as the original data. The output of the amplifier circuit 146 is applied to the horizontal input of the oscilloscope 31 via pole "b" of the selector switch 135, and is also applied to the amplifiers of the blanking circuit 151, which produces retrace blanking pulses applied to the blanking input of the oscilloscope via the pole "a" of the switch 135, in the same manner as was described above with respect to the blanking circuit 150. The output of the amplifier circuit 147 is applied to one input of the summer 149, the other input of which receives the output of the amplifier circuit 148. The summer 149 serves the same function as the summer 134, and its output is applied to the vertical input of the oscilloscope 31 via pole "c" of the switch 135.

When the inspection scan is completed, the switch 35 is moved back to its OFF position to de-energize the gearmotor 81. At this point, the shaft 85 should be in its fully retracted position. If the scan had been conducted in reverse order, i.e., during the upward spiral of the shaft 85, the shaft 85 would now have to be retracted before shut down of the insertion tool 60. The switch 37 is then actuated to de-energize the solenoid valve 122. This permits the coupling fluid to drain from the tube 26 back down through the outlet orifice 43 in the probe assembly 40, the tubular member 41, the flexible drive shaft 55, the drive shaft 85, the jacket 95, the conduit 120, the valve 122 and the conduit 123 to the container 113, by gravity. When the coupling fluid has been drained from the tube 26 and the insertion tool 60, the switch 38 is opened to de-energize the control and data handling circuit 130.

The operator then reenters the primary chamber 24, throws the toggle switch 98a on the insertion tool housing 62 to retract the cam lock plungers 72, and then removes the insertion tool 60 and the associated probe assembly 40 from the tube sheet 25 and the tube 26. The length of the flexible drive shaft 55 is then adjusted by adding or removing sections to bring it to the appropriate length for inspection of the next region of the tube 26 just inspected, or some other tube 26. The insertion tool 60 is then remounted in position for the next inspection scan and the process is repeated.

The plot displayed on the oscilloscope 31, as illustrated in FIG. 15, constitutes a pseudo-isometric map of tube wear. This analog display provides a convenient format for data interpretation but, if desired, further computer processing of the data can be effected, using a computer terminal 175 (FIG. 2) (either in real time or after taped delayed), to yield an actual three-dimensional contour map which, in turn, is the basis for volumetric measurements of the amount of material lost from the tube wall 27. A listing for a computer program for such further data processing is set forth in Table I at the end of this specification. This program is intended to be used for processing data received from the tape recorder 158, and it assumes that the recorded data has been digitized and stored in a file with the appropriate name, so that the data can be identified as to row, column, steam generator number etc. To facilitate discussion, different sections of the program have been designated.

Section 1 of the program reads the data file into memory and converts it from 12 bit 2's complement to 16 bit 2's complement. Section 2 scans the stored file and removes "tape dropouts" which are occasionally introduced by the tape recording process, due to lost or missing oxide on the tape. In Section 3, the corrected file is then scanned to locate all of the transitions of the angular position encoder saw tooth voltage. Having identified all of the transitions, Section 4 creates a new array whose indices correspond to angular and axial positions. It is this array which is used for all subsequent processing.

In Section 5, a 30-line, high resolution, pseudoisometric plot is processed. In Section 6, the operator selects a reference line which defines the nominal wall thickness as a function of angle. All measurements of wall thickness are compared to this reference. In Section 6A, the operator selects up to five regions of the scan for which the maximum depth of wall scar and total volume of material removed are calculated in Section 7. The final output is produced in Section 8, which includes the calculated depth, the volume of the material lost, and a color-coded C-scan plot, with the colors indicating wall thickness, which plot may be displayed on the computer terminal screen.

The inspection system 20 has been found to be capable of resolving tube thinning on the order of 0.0005 inch deep in a 0.043 inch thick tube wall. This represents an order of magnitude improvement over prior systems which were unreliable in detecting discontinuities with dimensions less than about 10% of the tubing wall thickness.

From the foregoing, it can be seen that there has been provided an improved inspection system which utilizes ultrasonic techniques, is characterized by great sensitivity and accuracy, and which is capable of producing accurate maps of areas of tube thinning and processing the data to provide measurements of the volume of material lost.

TYPE TKNESS.FOR  TABLE I
       PROGRAM TKNESS
C      ******** ARRAY CONFIGURATION BY COLUMN ********
C
C Col 1.     Col 2.      Col 3.         Col 4.
C  horz      thickness   Axial loc.      zero
C
       DIMENSION IDAT(80000,4),LOCTRN(100),NEWDAT(300,70,3),JSPAN(100)
       DIMENSION ITHK(300,70),CORR(300),VOL(8),DEPTH(8)
       INTEGER*2 IRDAT(256),CLEAR(80)
       INTEGER YMAX(300),YMIN(300),ITX(10),ITY(10),YINC
       INTEGER YREF,XREF,IBX(2),IBY(2)
       CHARACTER*14 FILE
       CHARACTER*24 DATE
       CALL SYS$ASCTIM(,DATE,,)
       DATA IRDAT/256*0/
       DATA IDAT/320000*0/
       DATA VOL/8*0/
C FVOL=PI*.7/(300*28)
C      FVOL=2.199E-04 IN ERROR DUE TO WRONG SPACING BETWEEN SCANS
       FVOL=2.618E-04
       DO 10 I=1,80
10     CLEAR(I)=' '
C
C **************************************************************************
C This section asks for the file name and checks to see if the calibration
C data is available. If not, program pauses.
C
       TYPE 900                    !Ask for file name.
       ACCEPT 910,FILE             !Accept file name.
C TO CONVERT THE CORRECTED THICKNESS ARRAY TO ACTUAL WALL LOSS THE EQN.
C      WALL=SLOPE*ITHK+BSETT
       vslope=1.4E-05
       O=INDEX(FILE,':')
       O=O+8    !Set O to first character after '.'
       O1=O+2
       IF (('FILE(O:O1) .EQ. '1D1') .OR. (FILE(O:O1) .EQ. '1DR') .OR.
      1   (FILE(O:O1) .EQ. '1D2') .OR. (FILE(O:O1) .EQ. '1D3')) THEN
       SLOPE=1.29E-05
       BSETT=-8.19E-04
       ELSE IF ((FILE(O:O1) .EQ. '1G1') .OR. (FILE(O:O1) .EQ. '1G2')
      1.OR. (FILE(O:O1) .EQ. '1GR')) THEN
C      SLOPE=1.29E-05
C      BSETT=-1.065E-3
       SLOPE=1.32E-05
       BSETT=-6.27E-4
       ELSE
C      PAUSE 'Calibration data not available'
       TYPE 9777
9777   FORMAT (1X, 'Specific calibration data not available - using 1D
      1 cal. data.')
       SLOPE=1.29E-05   !1D slope
       BSETT=-8.19E-04  !1D Bsett
C      SLOPE=1.32E-05   !1G slope
C      BSETT=-6.27E-04  !1G BSETT
       END IF
C ------------------------------------------------------------------------
C The following line of code opens the data file specified.
C If file is not found or a read error occurs, the program stops and an
C error message is printed.
C
       OPEN (UNIT=1, ACCESS='DIRECT',ASSOCIATEVARIABLE=IREC,
      1FILE=FILE,READONLY,RECL=128,STATUS='OLD',ERR=500)
       IREC=1                      !Set file pointer at 1.
       DO 100 I=1,10000            !Read the data file in groups-
       READ (1'IREC,ERR=200) IRDAT  !of 256.
       IDATA=0
       DO 120 K=1,64
       DO 110 J=1,4
       K1=(IREC-2)*64+K            !Row pointer for main array.
       IDAT(K1,J)=IRDAT(J+IDATA) .AND. "7777   !Only 12 bits
       IF ((IDAT(K1,J) .AND. "4000).GT.0) IDAT(K1,J)=IDAT(K1,J)-4096
```

```
110     CONTINUE
        IDATA=IDATA+4
120     CONTINUE
100     CONTINUE
200     CLOSE (UNIT=1)                    !Close the LUN.
        IPOITS=(IREC-1)*64                !Number of records read.
        K1=IPOITS
C
C End of file read
C ------------------------------------------------------------------------
C Loop 210 checks backwards from the end of the IDAT array. If the first two
C column entries are zero, it is assumed that the rest of the row is zero, and
C therefore not real data. The first non-zero entry encountered then indicates
C the last row of valid data.
C
        DO 210 I=K1,K1-128,-1
        IF (IDAT(I,1) .NE. 0) GO TO 220
210     IF (IDAT(I,2) .NE. 0) GO TO 220
C ------------------------------------------------------------------------
        STOP 'Error on detecting end of data stream in final array.'
220     IPOITS=I                          !Located end of record in array.
        TYPE 201,IPOITS                   !Print number of good records.
201     FORMAT (1X,'Number of records read = ',I12)
C       DO 1201 IIA=1,1000,2
C1201    TYPE 1200,IIA,IDAT(IIA,1),IDAT(IIA,2),IDAT(IIA,3),IDAT(IIA,4),
C       1IIA+1,IDAT(IIA+1,1),IDAT(IIA+1,2),IDAT(IIA+1,3),IDAT(IIA+1,4)
C1200    FORMAT(1X,10I6)
        GO TO 1203
500     STOP 'Error in file open sequence'
900     FORMAT (1H$,'What is the file name you wish to
        1 examine ? ')
910     FORMAT (A14)
1203    CONTINUE
        IDEL=100
        IDEL1=250
        ILENG=10
        DO 1305 K=2,4
        INTAL=IDAT(1,K)
        DO 1305 I=2,IPOITS
        IF (ABS(IDAT(I,K)-INTAL).GT.IDEL) GO TO 1300
        INTAL=IDAT(I,K)
        GO TO 1305
1300    IDUM=0
        DO 1302 ITEST=0,ILENG
        IF (ABS(IDAT(I+ITEST,K)-INTAL).LT.IDEL) GO TO 1302
        IDUM=IDUM+1
1302    CONTINUE
        IF (IDUM.GE.11) GO TO 1309
        DO 1308 ITEST=0,ILENG
        IF (ABS(IDAT(I+ITEST,K)-INTAL).LT.IDEL) GO TO 1308
        IDAT(I+ITEST,K)=INTAL
1308    CONTINUE
C       TYPE 1500,K,I,IDUM
1500    FORMAT(1X,'A tape dropout in channel ',I2,' at',I6,' for '
        1,I3,' points....REPLACED')
        GO TO 1305
1309    CONTINUE
C       TYPE 1502,K,I,IDUM
        INTAL=IDAT(I,K)
1502    FORMAT(1X,'A tape dropout in channel ',I2,' at',I6,' for '
        1,I3,' points....NOT REPLACED')
1305    CONTINUE
        ITRANS=0
        K=1
        INTAL=IDAT(1,1)
        DO 1350 I=2,IPOITS
        ITEMP=ABS(IDAT(I,1)-INTAL)
        IF(ITEMP.GT.IDEL1) GO TO 1340
        INTAL=IDAT(I,1)
        GO TO 1350
1340    CONTINUE
C1340   IF(IDAT(I,1).LT.-1600) GO TO 1370
```

```
C              IF(ITEMP.LT.2000) GO TO 1370
C              ITRANS=ITRANS+1
C              LOCTRN(ITRANS)=I
C              INTAL=IDAT(I,1)
C              IF (ITRANS.GE.100) GO TO 1380
C              GO TO 1350
1370           IDUM=1
               ISTRN=0
               DO 1382 ITEST=1,ILENG
               ITRY=ABS(IDAT(I+ITEST,K)-INTAL)

IF (ITRY.LT.IDEL1) GO TO 1382
C
               IF(IDAT(I+ITEST,1).LT.-1600) GO TO 1377
               IF(ITRY.LT.2000) GO TO 1377
               ISTRN=1
1377           IDUM=IDUM+1
1382           CONTINUE
               IF (IDUM.GE.11) GO TO 1389
               DO 1388 ITEST=0,ILENG
               IF (ABS(IDAT(I+ITEST,K)-INTAL).LT.IDEL1) GO TO 1388
               IDAT(I+ITEST,K)=INTAL
1388           CONTINUE
C              TYPE 1500,K,I,IDUM
               GO TO 1350
1389           CONTINUE
               IF(ISTRN.EQ.0) GO TO 1345
               ITRANS=ITRANS+1
               LOCTRN(ITRANS)=I
               INTAL=IDAT(I+ITEST,1)
               IF (ITRANS.GE.100) GO TO 1380
               GO TO 1350
C              TYPE 1502,K,I,IDUM
1345           INTAL=IDAT(I,K)
1350           CONTINUE
1380           CONTINUE
!              TYPE 1560,ITRANS
1560           FORMAT(1X,'There are ',I3,' scans')
               IF((ITRANS.EQ.0).OR.(ITRANS.GT.100)) STOP 'More than 100 TRANS'
C              TYPE 1570
1570           FORMAT(1X,'TRANSITION          LOCATION          SCAN LENGTH')
C              DO 1390 IPRNT=1,ITRANS-1
C1390          TYPE 1580,IPRNT,LOCTRN(IPRNT),LOCTRN(IPRNT+1)-LOCTRN(IPRNT)
1580           FORMAT(5X,I3,12X,I6,3X,I6)
C CALCULATE LENGTH OF EACH SCAN IF DIFF>1/3 INITIAL END DATA
               ISPAN(1)=LOCTRN(2)-LOCTRN(1)
               LTEST=ISPAN(1)/3
               DO 2000 ICOMP=2,ITRANS-1
               ISPAN(ICOMP)=LOCTRN(ICOMP+1)-LOCTRN(ICOMP)
               IF(ABS((ISPAN(ICOMP))-ISPAN(1)) .GT. LTEST) GO TO 2001
2000           CONTINUE
2001           ITRANS=ICOMP-1
D              TYPE 1560,ITRANS
               IF ((ITRANS.GT.70).OR.(ITRANS.LT.10)) STOP 'Compr. to more than 70'
C CONDENSE ARRAY INTO 300 PTS. AVERRAGE PTS TO PRODUCE NEW ARRAY
               DO 2020 ICOMP=1,ITRANS
               FACTOR=ISPAN(ICOMP)/300.
               IAVER=FACTOR+1
               DO 2020 J=0,299
               ISTART=LOCTRN(ICOMP)+J*FACTOR
               DO 2020 ICH=1,3
               ITOTAL=0
               DO 2030 I=ISTART,ISTART+IAVER
               ITOTAL=ITOTAL+IDAT(I,ICH)
2030           CONTINUE
               NEWDAT(J+1,ICOMP,ICH)=ITOTAL/IAVER
2020           CONTINUE
               TYPE 1600
1600           FORMAT(1x,'DATA COMPRESSION COMPLETE')
C              DO 2050 ICOMP=1,ITRANS
C              DO 2050 J=1,10
C2050          TYPE 1690,ICOMP,J,NEWDAT(J,ICOMP,1)
```

```
          DO 2040 ICOMP=2,ITRANS
          DO 2040 J=1,300
          ITEMP=NEWDAT(J,ICOMP,1)-NEWDAT(J,1,1)
          IF(ABS(ITEMP).LE.20) GO TO 2040
C         TYPE 1690,ICOMP,J,ITEMP
1690      FORMAT(1X,'scan line',I4,5X,'location',I4,5X,'error',I6)
2040      CONTINUE
C ------------------------------------------------------------------
C
C This is the plotting section of the wear scar program.
C Part #1 draws the pseudo-isometric projection using the raw data
C in the NEWDAT array.
C PART #1
C
          CALL TK4010                         !Set to 4010 type
          CALL CLDIAG                         !Clear dialog area
          CALL PAGE                           !Clear graphics area
          CALL COLORM (0,0,0,0)               !Set background to black.
          CALL COLORM (1,10,100,0)            !White
          CALL COLORM (2,120,50,100)          !Red
          CALL COLORM (3,160,50,100)          !Orange
          CALL COLORM (5,300,50,100)          !Lt Blue
          CALL COLORM (4,180,50,100)          !Yellow
          CALL COLORM (6,240,80,50)           !Med green
          CALL COLORM (7,240,50,100)          !Dark green
          CALL TSEND                          !Dump buffer
          CALL GRMODE                         !Call graphic mode
          CALL STLINE (7)                     !Call Green
          IPINC=11
          IF (ITRANS .GT. 30) THEN
          YINC=2500/ITRANS
          INIT=NEWDAT(1,ITRANS,2)/2
          IYOFF=3000-((ITRANS*YINC)+INIT)
          IXOFF=500                           !Set X offset
          DO 5101 I=1,ITRANS                  !For first value in each row,
          IY=(I*YINC)+IYOFF+(NEWDAT(1,I,2)/2) !find Y position and
          IX=IXOFF                            !X position (+10) for mult fac.
          CALL MOVE (IX,IY)                   !& move there.
          DO 5101 J=2,300,IPINC
          IY=(I*YINC)+IYOFF+(NEWDAT(J,I,2)/2) !Calc Y position.
          IX=(J-1)*10+IXOFF                   !Calc X position
          CALL DRAW (IX,IY)
5101      CONTINUE
          CALL TSEND                          !Dump buffer
5121      CALL MOVE (0,100)                   !Move to Lower Left
          ILINE=1
5122      IF (ILINE .EQ. 1) THEN
          CALL ALMODE                         !Call ALPHA MODE
          WRITE (5,9012)
9012      FORMAT (1H+,'Data file too large - Select bottom line of
          1 group to be scanned (MAX 30).',$)
          CALL GRMODE
          CALL MOVE (0,0)
          CALL ALMODE
          WRITE (5,9011)
9011      FORMAT (1H+,'Position cursor on selected base line ',$)
          ELSE
          CALL GRMODE
          CALL MOVE (0,100)
          CALL ALMODE
          WRITE (5,9020) (CLEAR(I),I=1,78)
          WRITE (5,9013)
9013      FORMAT (1H+,'Select Upper line of range to be scanned.',$)
          CALL GRMODE
          CALL MOVE (0,0)
          CALL ALMODE
          WRITE (5,9020) (CLEAR(I),I=1,78)
          WRITE (5,9013)
          END IF
          CALL GRMODE                         !Call GRAPHIC MODE
          CALL GIN (I1,I2)                    !Graphic input position
C
```

```
C The following section of code determines the row from the array to use
C for reference data, and re-draws the line in red for clarification.
C
        XREF=(I1-IXOFF)/10              !Calc array row
        YREF=I2                         !Save Y position
C
C TRY TO FIX HIGHEST Y
        YTOP=(ITRANS*YINC)+IYOFF+(NEWDAT(1,ITRANS,2)/2)
        IF (YREF .GT. YTOP) YREF=YTOP
C
        IREFL=1
        IMINY=5000
        DO 5131 K=1,ITRANS
        ITEMP=(K*YINC)+IYOFF+(NEWDAT(XREF,K,2)/2)
        IF (ABS(YREF-ITEMP) .LT. IMINY) THEN
        IMINY=ABS(YREF-ITEMP)
        IF (ILINE .EQ. 1) ISTRT=K
        IF (ILINE .GT. 1) ISTOP=K
        IF (ISTOP .GT. (ISTRT+30)) ISTOP=ISTRT+30
        IF (ISTOP .GT. ITRANS) ISTOP=ITRANS
        END IF
5131    CONTINUE
C
C End of row index determination
C
C The next section re-draws the line in red. -
C
        CALL STLINE (2)                         !Set line to red.
        IF (ILINE .EQ. 1) ICOL=ISTRT
        IF (ILINE .GT. 1) ICOL=ISTOP
        IY=(ICOL*YINC)+IYOFF+(NEWDAT(1,ICOL,2)/2)    !First value in column
        IX=IXOFF
        CALL MOVE (IX,IY)
        DO 5141 J=2,300,IPINC
        IY=(ICOL*YINC)+IYOFF+(NEWDAT(J,ICOL,2)/2)
        IX=(J-1)*10+IXOFF
        CALL DRAW (IX,IY)
5141    CONTINUE
C
C Reference line has been redrawn, ask if correct.
C
        CALL ALMODE
        CALL GRMODE
        CALL MOVE (0,0)
        CALL ALMODE
        WRITE (5,9020) (CLEAR(I),I=1,78)
        CALL GRMODE
        CALL MOVE (0,0)
        CALL ALMODE
        WRITE (5,9050)
        READ (5,9060) IDUMM
        CALL GRMODE
        IF (IDUMM .EQ. 'N' .OR. IDUMM .EQ. 'n') THEN
C
C If not correct, re-draw line in green, & so ask again.
C
        CALL STLINE (7)
        IY=(ICOL*YINC)+IYOFF+(NEWDAT(1,ICOL,2)/2)
        IX=IXOFF
        CALL MOVE (IX,IY)
        DO 5151 J=2,300,IPINC
        IY=(ICOL*YINC)+IYOFF+(NEWDAT(J,ICOL,2)/2)
        IX=(J-1)*10+IXOFF
        CALL DRAW (IX,IY)
5151    CONTINUE
        CALL MOVE (0,0)
        CALL ALMODE
        WRITE (5,9020) (CLEAR(I),I=1,78)
        CALL GRMODE
        IF (ILINE .EQ. 1) THEN
        GO TO 5121
        ELSE
        GO TO 5122
```

```
              END IF
              END IF
              IF (ILINE .LT. 2) THEN
C*********
C*********
C REDRAW 30+ line in blue
              CALL STLINE (5)
              IHIY=ICOL+30
              CALL ALMODE
              CALL GRMODE
              IF (IHIY .GT. ITRANS) IHIY=ITRANS
              IY=(IHIY*YINC)+IYOFF+(NEWDAT(1,IHIY,2)/2)
              IX=IXOFF
              CALL MOVE (IX,IY)
              DO 15150 J=2,300,IPINC
              IY=(IHIY*YINC)+IYOFF+(NEWDAT(J,IHIY,2)/2)
              IX=(J-1)*10+IXOFF
              CALL DRAW (IX,IY)
15150         CONTINUE
              CALL MOVE (0,0)
              CALL STLINE (7)
C*********
              ILINE=ILINE+1
              GO TO 5122
              END IF
C
C If selected line is correct, continue.
C
              CALL PAGE                    !ERASE
              CALL STLINE (7)              !Call Green
              ELSE         !Alternate  (ITRANS <= 30)
              ISTRT=1
              ISTOP=ITRANS
              END IF            !End of IF for ITRANS>30
C
C Start of final form plotting section
C
              YINC=60                      !Set vertical increment/each line
              INIT=0
              DO 7766 K41=1,300
7766          IF (NEWDAT(K41,ISTOP,2) .GT. INIT) INIT=NEWDAT(K41,ISTOP,2)
C             INIT=NEWDAT(1,ISTOP,2)/2     !First point on last line
              INIT=INIT/2
C
C Calculate Vertical offset required to set scan near top of tube (~3100
C maximum) Number of lines (ITRANS) times the vertical increment (YINC)
C plus the initial signal height (INIT), all subtracted from 3000.
C
              IYOFF=3000-((ISTOP*YINC)+INIT)
C**** CHANGED IXOFF from 0 to 50*********************************
              IXOFF=50                     !Set X offset
              CALL PAGE
C             DO 5000 I=1,300              !Use first column of data to-
C             YMAX(I)=YINC*ISTRT+IYOFF+(NEWDAT(I,ISTRT,2)/2)
C5000         YMIN(I)=YMAX(I)              !hidden line checks.
              DO 5100 I=ISTRT,ISTOP        !For first value in each row,
              IY=(I*YINC)+IYOFF+(NEWDAT(1,I,2)/2)   !find Y position and
              IX=IXOFF                     !X position
              CALL MOVE (IX,IY)            !& move there.
              IPINC=1                      !Plotting increment thru 300 points
              DO 5110 J=2,300,IPINC
              IXEND=J                      !Save last J for later.
              IY=(I*YINC)+IYOFF+(NEWDAT(J,I,2)/2)   !Calc Y position.
              IX=(J-1)*10+IXOFF            !Calc X position
C             IF (IY .GE. YMAX(J)) THEN    !If not hidden, then-
              CALL DRAW (IX,IY)
C             YMAX(J)=IY
C             ELSE IF (IY .LE. YMIN(J)) THEN   !If not hidden, then-
C             CALL DRAW (IX,IY)            !draw the segment &-
C             ELSE
C             CALL MOVE (IX,IY)            !Must be hidden, just move.
C             END IF
5110          CONTINUE
```

```
5100    CONTINUE
        CALL TSEND                                      !Dump buffer
5120    CALL MOVE (0,0)                                 !Move to Lower Left
        CALL ALMODE                                     !Call ALPHA MODE
        WRITE (5,9010)
9010    FORMAT (1H+,'Position cursor on selected reference line ',$)
        CALL GRMODE                                     !Call GRAPHIC MODE
        CALL GIN (I1,I2)                                !Graphic input position
C
C The following section of code determines the row from the array to use
C for reference data, and re-draws the line in red for clarification.
C
        XREF=(I1-IXOFF)/10                  !Calc array row
        YREF=I2                             !Save Y position
        IREFL=1
        IMINY=5000
        DO 5130 K=ISTRT,ISTOP
        ITEMP=(K*YINC)+IYOFF+(NEWDAT(XREF,K,2)/2)
        IF (ABS(YREF-ITEMP) .LT. IMINY) THEN
        IMINY=ABS(YREF-ITEMP)
        IREFL=K
        END IF
5130    CONTINUE
C
C End of row index determination
C
C The next section re-draws the line in red.
C
        CALL STLINE (2)                                 !Set line to red.
        IY=(IREFL*YINC)+IYOFF+(NEWDAT(1,IREFL,2)/2)     !First value in column
        IX=IXOFF
        CALL MOVE (IX,IY)
        DO 5140 J=2,300,IPINC
        IY=(IREFL*YINC)+IYOFF+(NEWDAT(J,IREFL,2)/2)
        IX=(J-1)*10+IXOFF
        CALL DRAW (IX,IY)
5140    CONTINUE
C
C Reference line has been redrawn, ask if correct.
C
        CALL ALMODE
        CALL GRMODE
        CALL MOVE (0,0)
        CALL ALMODE
        WRITE (5,9020) (CLEAR(I),I=1,78)
        CALL GRMODE
        CALL MOVE (0,0)
        CALL ALMODE
        WRITE (5,9050)
9050    FORMAT (1H+,'Correct (Y or N) (Default = Y) ? ',$)
        READ (5,9060) IDUMM
        CALL GRMODE
        IF (IDUMM .EQ. 'N' .OR. IDUMM .EQ. 'n') THEN
C
C If not correct, re-draw line in green, & go ask again.
C
        CALL STLINE (7)
        IY=(IREFL*YINC)+IYOFF+(NEWDAT(1,IREFL,2)/2)
        IX=IXOFF+10
        CALL MOVE (IX,IY)
        DO 5150 J=2,300,IPINC
        IY=(IREFL*YINC)+IYOFF+(NEWDAT(J,IREFL,2)/2)
        IX=(J-1)*10+IXOFF
        CALL DRAW (IX,IY)
5150    CONTINUE
        CALL MOVE (0,0)
        CALL ALMODE
        WRITE (5,9020) (CLEAR(I),I=1,78)
        CALL GRMODE
        GO TO 5120
        END IF
```

SEC.6A

```
C
C If selected line is correct, continue.
C
        CALL STLINE (1)         !Set graphics lines to white
        CALL MOVE (0,0)
        CALL ALMODE
        WRITE (5,9020) (CLEAR(I),I=1,78)
9020    FORMAT (1H+,78A1,$)
        CALL GRMODE
        CALL MOVE (0,500)
        CALL ALMODE
        WRITE (5,9030)
9030    FORMAT (1H+,'Select Graphic pointers in groups of two.',$)
        CALL GRMODE
        CALL MOVE (0,400)
        CALL ALMODE
        WRITE (5,9031)
9031    FORMAT (1H+,'LOWER LEFT then UPPER RIGHT.',$)
        INUM=0                  !Initialize counter for X's & Y's
5160    CALL GRMODE
        CALL MOVE (0,0)
C The following section of code determines the row (ITX) and column (ITY)
C from the array to use for volume calculations. These values are acquired
C in pairs of pairs (four values) and stored in ITX and ITY arrays. The
C variable INUM contains the number of values in the arrays. Note that INUM
C is always a multiple of 2.
C
        IF (INUM .LT. 2) CALL STLINE (1)
        IF (INUM .GE. 2 .AND. INUM .LT. 4) CALL STLINE (2)
        IF (INUM .GE. 4 .AND. INUM .LT. 6) CALL STLINE (3)
        IF (INUM .GE. 6 .AND. INUM .LT. 8) CALL STLINE (5)
        IF (INUM .GE. 9) CALL STLINE (6)
        DO 5170 I=1,2            !Loop to set X's & Y's for volume calc's.
        INUM=INUM+1
        CALL GIN (I1,I2)         !Set cursor position
        IBX(I)=I1                !Save cursor X position for later draw.
        IBY(I)=I2                !Save cursor Y position for later draw.
        CALL MKMODE              !Enter mark mode
        CALL MRKTYP (2)          !Select marker type
        CALL DRWMRK (I1,I2)      !Draw marker
        CALL ALMODE              !Must go to Alpha mode first
        CALL GRMODE              !Then graph mode
        ITX(INUM)=(I1-IXOFF)/10  !Calc array row
        XREF=ITX(INUM)
        YREF=I2                  !Save Y position
        ITY(INUM)=1
        IMINY=5000
        DO 5180 K=ISTRT,ISTOP
        ITEMP=(K*YINC)+IYOFF+(NEWDAT(XREF,K,2)/2)
        IF (ABS(YREF-ITEMP) .LT. IMINY) THEN
        IMINY=ABS(YREF-ITEMP)
        ITY(INUM)=K
        END IF
5180    CONTINUE
5170    CONTINUE
C
C End of row index determination
C                                                                         SEC.6A
        CALL LNSTYL (7) !DASHED LINE
        IXMIN=IBX(1)
        IYMIN=IBY(1)
        IXMAX=IBX(2)
        IYMAX=IBY(2)
        IF (IBX(1) .LT. IBX(2)) THEN
        CALL MOVE (IXMIN,IYMIN)
        CALL DRAW (IXMAX,IYMIN)
        CALL DRAW (IXMAX,IYMAX)
        CALL DRAW (IXMIN,IYMAX)
        CALL DRAW (IXMIN,IYMIN)
        ELSE
        CALL MOVE (IXOFF+IXEND*10,IYMIN)
        CALL DRAW (IXMIN,IYMIN)
        CALL DRAW (IXMIN,IYMAX)
```

```
              CALL DRAW (IXOFF+IXEND*10,IYMAX)
              CALL MOVE (IXOFF+10,IYMIN)
              CALL DRAW (IXMAX,IYMIN)
              CALL DRAW (IXMAX,IYMAX)
              CALL DRAW (IXOFF+10,IYMAX)
              END IF
              CALL MOVE (0,0)
              IF (INUM .GE. 10) GO TO 6452
              CALL ALMODE
              WRITE (5,9040)
 9040         FORMAT (1H+,'Another group (Default = N) (Y or N) ? ',$)
              READ (5,9060) IDUMM
 9060         FORMAT (1A1)
              CALL GRMODE
              CALL MOVE (0,0)
              CALL ALMODE
              WRITE (5,9020) (CLEAR(K),K=1,78)
              IF (IDUMM .EQ. 'Y' .OR. IDUMM .EQ. 'y') GO TO 5160
 6452         CALL GRMODE                              !Set GRAPHICS MODE
              CALL MOVE (0,500)                        !Move to 0,500
              CALL ALMODE                              !Call ALPHA MODE
              WRITE (5,9020) (CLEAR(K),K=1,78)         !Erase line
              CALL GRMODE                              !Set GRAPHICS MODE
              CALL MOVE (0,400)                        !Move to 0,400
              CALL ALMODE                              !Set ALPHA MODE
              WRITE (5,9020) (CLEAR(K),K=1,78)         !Erase line.
C
C     EXTENT OF TUBE TO CALCULATE CORRECTION TO VOLUME LOST
C  2-14-83 CHANGE TO ADOPT NEW UPPER LINE DEFINITION ISTOP
C
c             JYLMAX=0
c             DO 10000 III=2,INUM,2
c             IF(ITY(III).lt.JYLMAX) go to 10000
c             JNUMX=III
c             JYLMAX=ITY(III)
c10000        continue
C
C  CALCULTE CORRECTION DUE TO BASE LINE DRIFT
C
              DO 10100 I=1,300
10100         CORR(I)=(FLOAT(NEWDAT(I,istop,2)-NEWDAT(I,IREFL,2))
              1/FLOAT(istop-IREFL))
c10100        CORR(I)=(FLOAT(NEWDAT(I,ITY(JNUMX),2)-NEWDAT(I,IREFL,2))
c             1/FLOAT(ITY(JNUMX)-IREFL))
C
C  ESTABLISH NEW THICKNESS ARRAY CORRECTED FOR DRIFT AND CONCENTRICITY
C
              DO 10200 I=1,300
              DO 10200 J=ISTRT,ISTOP
10200         ITHK(I,J)=(NEWDAT(I,J,2)-NEWDAT(I,IREFL,2))-CORR(I)*(J-IREFL)
C
C  CALCULATE NORMALIZED VOLUME
C
              IVOL=0.
              DO 10320 INUMTM=2,INUM,2
              IVOL=IVOL+1
              IDEEP=0
              IF(ITX(INUMTM).LT.ITX(INUMTM-1)) GO TO 10250
              DO 10201 I=ITX(INUMTM-1),ITX(INUMTM)
              DO 10201 J=ITY(INUMTM-1),ITY(INUMTM)
              IF(ITHK(I,J).LT.IDEEP) IDEEP=ITHK(I,J)
10201         VOL(IVOL)=ITHK(I,J)*VSLOPE+VOL(IVOL)
c10201        VOL(IVOL)=ITHK(I,J)*SLOPE+BSETT+VOL(IVOL)
              DEPTH(IVOL)=IDEEP*SLOPE+BSETT
              GO TO 10300
10250         DO 10260 I=ITX(INUMTM-1),300
              DO 10260 J=ITY(INUMTM-1),ITY(INUMTM)
              IF(ITHK(I,J).LT.IDEEP) IDEEP=ITHK(I,J)
10260         VOL(IVOL)=ITHK(I,J)*VSLOPE+VOL(IVOL)
C10260        VOL(IVOL)=ITHK(I,J)*SLOPE+BSETT+VOL(IVOL)
              DO 10270 I=1,ITX(INUMTM)
              DO 10270 J=ITY(INUMTM-1),ITY(INUMTM)
              IF(ITHK(I,J).LT.IDEEP) IDEEP=ITHK(I,J)
```

```
10270       VOL(IVOL)=ITHK(I,J)*VSLOPE+VOL(IVOL)
C10270      VOL(IVOL)=ITHK(I,J)*SLOPE+BSETT+VOL(IVOL)
            DEPTH(IVOL)=IDEEP*SLOPE+BSETT
10300       CONTINUE
9000        FORMAT (I1)
C           WRITE (5,9020) (CLEAR(K),K=1,78)
10320       CONTINUE
C
C Next section draws the color map
C
            CALL GRMODE
C-          K5=(-.001-BSETT)/SLOPE
            K5=(-.0013-BSETT)/SLOPE
            K4=(-.003-BSETT)/SLOPE
            K3=(-.005-BSETT)/SLOPE
            K2=(-.008-BSETT)/SLOPE
            K1=(-.011-BSETT)/SLOPE
            IYOFF=500
            CALL GAMODE (1)
C
C Loop 20110 is the loop which draws the color C-scan at the bottom of the
C screen. ISTRT and ISTOP are column numbers for the ITHK array which will
C be plotted. The screen height of each horizontal trace is set by the value
C of IYMULT.
C
            IYOFF=30
            IYMULT=30
            DO 20110 J=ISTRT,ISTOP
            IY=(J-ISTRT)*IYMULT+IYOFF
            IX0=IXOFF
            NUM=ITHK(1,J)
            IF (                         NUM .LT. K1) LFILL0=2
            IF (NUM .GE. K1 .AND. NUM .LT. K2) LFILL0=3
            IF (NUM .GE. K2 .AND. NUM .LT. K3) LFILL0=4
            IF (NUM .GE. K3 .AND. NUM .LT. K4) LFILL0=5
            IF (NUM .GE. K4 .AND. NUM .LT. K5) LFILL0=6
            IF (NUM .GE. K5                  ) LFILL0=7
            DO 20100 I=2,300
            NUM=ITHK(I,J)
            IF (                         NUM .LT. K1) LFILL=2
            IF (NUM .GE. K1 .AND. NUM .LT. K2) LFILL=3
            IF (NUM .GE. K2 .AND. NUM .LT. K3) LFILL=4
            IF (NUM .GE. K3 .AND. NUM .LT. K4) LFILL=5
            IF (NUM .GE. K4 .AND. NUM .LT. K5) LFILL=6
            IF (NUM .GE. K5                  ) LFILL=7
            IF ((LFILL .NE. LFILL0) .OR. (I .EQ. 300)) THEN
            IX=(I*10)+IXOFF
            CALL FILPNL (-LFILL0)
            CALL BEGPNL (IX0 ,IY,0)
            CALL MOVE    (IX  ,IY)
            CALL MOVE    (IX  ,IY+IYMULT)
            CALL MOVE    (IX0 ,IY+IYMULT)
            CALL ENDPNL
            IX0=IX
            LFILL0=LFILL
            ENDIF
20100       CONTINUE
20110       CONTINUE
            CALL STLINE (1)
            CALL MOVE (IXOFF,IYOFF)
            CALL DRAW (3000+IXOFF,IYOFF)
            CALL DRAW (3000+IXOFF,(ISTOP-ISTRT)*IYMULT+IYOFF+IYOFF)
            CALL DRAW (IXOFF,(ISTOP-ISTRT)*IYMULT+IYOFF+IYOFF)
            CALL DRAW (IXOFF,IYOFF)
            IX=3100+IXOFF
            DO 20200 I=2,7
            LFILL=I
            IYOFF=100
            IXOFF=50
            CALL FILPNL(-LFILL)
            IY=IYOFF+(I-2)*100
            CALL BEGPNL (IX,IY,1)
            CALL MOVE (IX+60,IY)
```

SEC. 8

```
              CALL MOVE (IX+60,IY+60)
              CALL MOVE (IX,IY+60)
              CALL ENDFNL
20200         CONTINUE
              IX=3200+IXOFF
              CALL MOVE (IX,IYOFF+100)
              CALL ALMODE
              CALL TXTIND (1)
              WRITE (5,90200)
90200         FORMAT (1H+,'= > 0.011"',$)
              CALL GRMODE
              CALL MOVE (IX,IYOFF+200)
              CALL ALMODE
              CALL TXTIND (1)
              WRITE (5,90210)
90210         FORMAT (1H+,'= 0.011 - 0.008"',$)
              CALL GRMODE
              CALL MOVE (IX,IYOFF+300)
              CALL ALMODE
              CALL TXTIND (1)
              WRITE (5,90220)
90220         FORMAT (1H+,'= 0.008 - 0.005"',$)
              CALL GRMODE
              CALL MOVE (IX,IYOFF+400)
              CALL ALMODE
              CALL TXTIND (1)
              WRITE (5,90230)
90230         FORMAT (1H+,'= 0.005 - 0.003"',$)
              CALL GRMODE
              CALL MOVE (IX,IYOFF+500)
              CALL ALMODE
              CALL TXTIND (1)
              WRITE (5,90240)
90240         FORMAT (1H+,'= 0.003 - 0.001"',$)
              CALL GRMODE
              CALL MOVE (IX,IYOFF+600)
              CALL ALMODE
              CALL TXTIND (1)
              WRITE (5,90250)
90250         FORMAT (1H+,'= < 0.001"',$)
              CALL MOVE (IX,IYOFF+750)
              CALL ALMODE
              CALL TXTIND (1)
              WRITE (5,90260)
90260         FORMAT (1H+,'     LEGEND',$)
              CALL MOVE (IX,IYOFF+650)
              WRITE (5,90270)
90270         FORMAT (1H+,'      _____',$)
              IX=3020+IXOFF
              ITOP=2700
              CALL MOVE (IX+150,ITOP+300)
              WRITE (5,90272) DATE(1:11)
90272         FORMAT (1H+,A11,$)
              CALL MOVE (IX+150,ITOP+300)
              WRITE (5,90274)
90274         FORMAT (1H+,'_____',$)
              CALL MOVE (IX+175,ITOP+200)
C             WRITE (5,90276) FILE(0-7:01)
90276         FORMAT (1H+,A10,$)
              CALL MOVE (IX,ITOP)
              WRITE (5,90280)
              CALL MOVE (IX,ITOP-100)
              WRITE (5,90290) FILE(0:0)
              CALL MOVE (IX,ITOP-200)
C             WRITE (5,90300) FILE (0-6:0-5)
              WRITE (5,90300)
              CALL MOVE (IX,ITOP-300)
              WRITE (5,90310) FILE (0-3:0-2)
              WRITE (5,90310)
              CALL MOVE (IX,ITOP-400)
              WRITE (5,90320) FILE (0+1:0+1)
C90280        FORMAT (1H+,'Plant Name: KRSKO',$)
90280         FORMAT (1H+,'Plant Name:  XYZ  ',$)
```

```
90290      FORMAT (1H+,'Generator:    #',A1,$)
C90300     FORMAT (1H+,'Row:          #',A2,$)
90300      FORMAT (1H+,'Row:          #','99',$)
C90310     FORMAT (1H+,'Column:       #',A2,$)
90310      FORMAT (1H+,'Column:       #','99',$)
90320      FORMAT (1H+,'Support:      ',A1,$)
           IDOWN=ITOP-600
           CALL MOVE (IX,IDOWN)
           CALL ALMODE
           WRITE (5,90020)
           idown=idown-100
           CALL MOVE (IX,IDOWN)
           WRITE (5,90029)
           DO 6666 I=1,INUM/2
           IF (I .EQ. 1) CALL TXTIND (1)
           IF (I .EQ. 2) CALL TXTIND (2)
           IF (I .EQ. 3) CALL TXTIND (3)
           IF (I .EQ. 4) CALL TXTIND (5)
           IF (I .EQ. 5) CALL TXTIND (6)
90020      FORMAT (1H+,'Depth   Wear Volume',$)
90029      FORMAT (1H+,' IN.         CU. IN.',$)
           IDOWN=IDOWN-100
           CALL MOVE (IX,IDOWN)
           CALL ALMODE
           IF (ABS(VOL(I)) .LT. 9.9999999E-6) THEN
           WRITE (5,90022) DEPTH(I)
90022      FORMAT (1H+,F6.4,1X,'<-9.99E-06',$)
           ELSE IF (VOL(I) .GE. 0.0) THEN
           WRITE (5,90023) DEPTH(I)
90023      FORMAT (1H+,F6.4,2X,' 0.000',$)
           ELSE
           WRITE (5,90021) DEPTH(I),VOL(I)*FVOL
90021      FORMAT (1H+,F6.4,2X,1PE10.2,$)
           END IF
6666       CONTINUE
           CALL TXTIND (1)
           CALL STLINE (1)
C
           CALL GAMODE (0)
           CALL GRMODE
           CALL MOVE (0,0)
           CALL DRAW (4095,0)
           CALL DRAW (4095,3132)
           CALL DRAW (0,3132)
           CALL DRAW (0,0)
           CALL HDCOPY
           CALL ALMODE
           READ (5,9000) IDUMM
4000       CONTINUE
           STOP
           END
```

We claim:

1. A system for determination of the extent of erosion in a degraded area in the wall of a heat exchange tube of a nuclear system generator, said system comprising: ultrasonic means including transducer means and control means, said transducer means being responsive to said control means for emitting ultrasonic waves and receiving reflected waves generally parallel to an emission axis, drive means coupled to said transducer means for moving it axially and rotatably inside a tube along an inspection region with said emission axis disposed radially of the tube so that said emission axis describes a helical path along the tube wall, said control means being responsive to reflected ultrasonic waves from the inner and outer surfaces of the tube wall for producing a thickness signal indicative of the thickness of the tube wall, a reservoir containing a supply of coupling liquid through which ultrasonic waves can propagate with relatively low attenuation, pump means for transferring a quantity of said coupling liquid from said reservoir to the tube for filling the inspection region thereof and surrounding said transducer means to facilitate the transmission of ultrasonic waves between said transducer means and the tube wall, valve means for controlling the flow of coupling liquid from the tube to said reservoir, means for controlling the operation of said pump means and said valve means, said pump means and said valve means being connected in parallel between said reservoir and the tube, said valve means being closed when said pump means is operated and said pump means being deactuated when said valve means is open, means for producing position signals respectively indicative of the axial and angular position of said transducer means within the tube, and data handling means responsive to said thickness signal and to said position signals for producing a plot of the tube wall thickness around the entire circumference thereof along a predetermined axial extent thereof, thereby to provide a map of the tube wall thickness in the degraded area.

2. The system of claim 1, wherein said data handling means includes summing means for adding said thickness signal to said axial position signal.

3. The system of claim 2, wherein said data handling means includes means for doubling the amplitude of said thickness signal before addition to said axial position signal.

4. The system of claim 2, and further including storage means for said thickness signal and said position signals.

5. The system of claim 4, wherein said data handling means includes second summing means for adding the stored thickness signal to the stored axial position signal, and means for transferring said stored angular position signal and the output of said second summing means to said display means.

6. The system of claim 1, and further including computer means operable under the control of a stored program for operating on said position signals and said thickness signal to produce a three-dimensional contour map of the degraded area of the tube wall and compute the volume of material lost therefrom.

7. The system of claim 1, and further including seal means for preventing escape of said coupling liquid from the tube.

8. The system of claim 1, and further including means for venting said reservoir to atmosphere.

9. A system for determination of the extent of erosion in a degraded area in the wall of a heat exchange tube of a nuclear steam generator, said system comprising: ultrasonic means including probe means adapted to be moved within a tube and control means; said probe means including a hollow tubular member having an outlet orifice therein and having an outer diameter substantially less than the inner diameter of the associated steam generator tube, a plurality of resilient annular centering members carried by said tubular member and spaced apart longitudinally thereof and dimensioned for sliding engagement with the steam generator tube wall for centering said tubular member inside the steam generator tube, and ultrasonic transducer means carried by said tubular member; an elongated hollow flexible drive shaft having one end thereof communicating with said tubular member; means coupling said transducer means to said control means; said transducer means being responsive to said control means for emitting ultrasonic waves and receiving reflected waves generally parallel to an emission axis; drive means coupled to the other end of said drive shaft for moving said probe means axially and rotatably inside a tube along an inspection region with said emission axis disposed radially of the tube so that said emission axis describes a helical path along the tube wall; said control means being responsive to reflected ultrasonic waves from the inner and outer surfaces of the tube wall for producing a thickness signal indicative of the thickness of the tube wall; a reservoir containing a supply of coupling liquid through which ultrasonic waves can propagate with relatively low attenuation; means for transferring a quantity of said coupling liquid from said reservoir to said hollow drive shaft and thence to the tube for filling the inspection region thereof and surrounding said transducer means to facilitate the transmission of ultrasonic waves between said transducer means and the tube wall; means for producing position signals respectively indicative of the axial and angular position of said transducer means within the tube, and data handling means responsive to said thickness signal and to said position signals for producing a plot of the tube wall thickness around the entire circumference thereof along a predetermined axial extent thereof, thereby to provide a map of the tube wall thickness in the degraded area.

10. The system of claim 9, wherein said hollow tubular member includes a recessed portion for receiving said transducer means therein.

11. The system of claim 9, wherein each of said centering members has a plurality of radially outwardly extending resilient fingers disposed for sliding engagement with the inner surface of the associated steam generator tube.

12. The system of claim 9, and further including electrical connectors disposed within said drive shaft and said tubular member and interconnecting said transducer means and said control means.

* * * * *